(12) United States Patent
Inouye et al.

(10) Patent No.: US 8,816,052 B2
(45) Date of Patent: Aug. 26, 2014

(54) MUTANT APOPROTEIN OF PHOTOPROTEIN WITH LOW CALCIUM SENSITIVITY

(75) Inventors: Satoshi Inouye, Yokohama (JP); Yuiko Miura, Yokohama (JP)

(73) Assignee: JNC Corporation, Tokyo (JP)

( * ) Notice: Subject to any disclaimer, the term of this patent is extended or adjusted under 35 U.S.C. 154(b) by 75 days.

(21) Appl. No.: 13/430,914

(22) Filed: Mar. 27, 2012

(65) Prior Publication Data

US 2012/0258465 A1 Oct. 11, 2012

(30) Foreign Application Priority Data

Apr. 5, 2011 (JP) ................................. 2011-083968

(51) Int. Cl.
| | | |
|---|---|---|
| *C07K 1/00* | (2006.01) | |
| *C07K 14/435* | (2006.01) | |
| *C12Q 1/68* | (2006.01) | |
| *C12P 21/06* | (2006.01) | |
| *C07H 21/04* | (2006.01) | |

(52) U.S. Cl.
USPC ............ 530/350; 530/402; 435/6.15; 435/29; 435/69.1; 435/252.33; 435/320.1; 536/23.5

(58) Field of Classification Search
USPC ................. 435/6.15, 29, 69.1, 252.33, 320.1; 530/350, 402; 536/23.5
See application file for complete search history.

(56) References Cited

U.S. PATENT DOCUMENTS

2009/0203888 A1 8/2009 Golz et al.

FOREIGN PATENT DOCUMENTS

WO WO-03082904 A2 10/2003

OTHER PUBLICATIONS

Satoshi Inouye et al., "Cloning and sequence analysis of cDNA for the luminescent protein aequorin," Proc. Natl. Acad. Sci. USA, May 1985, vol. 82, pp. 3154-3158.
James F. Head et al., "The crystal structure of the photoprotein aequorin at 2.3 Å resolution," Nature, May 18 2000, vol. 405, pp. 372-376.
Frederick I. Tsuji et al., "Site-specific mutagenesis of the calcium-binding photoprotein aequorin," Proc. Natl. Acad. Sci. USA, Nov. 1986, vol. 83, pp. 8107-8111.
Kouichi Kurose et al., "Bioluminescence of the $Ca^{2+}$-binding photoprotein aequorin after cysteine modification," Proc. Natl. Acad. Sci. USA, Jan. 1989, vol. 86, pp. 80-84.
Jonathan M. Kendall et al., "Engineering the $Ca^{2+}$-Activated Photoprotein Aequorin With Reduced Affinity for Calcium," Biochemical and Biophysical Research Communications, Sep. 16, 1992, vol. 187, No. 2, pp. 1091-1097.
Yoshihiro Ohmiya et al., "Two excited states in aequorin bioluminescence induced by tryptophan modification," FEBS Lett., Apr. 1992, vol. 301, No. 2, pp. 197-201.
Yoshihiro Ohmiya et al., "Bioluminescence of the $Ca^{2+}$-binding photoprotein, aequorin, after histidine modification," FEBS Lett., Apr. 1993, vol. 320, No. 3., pp. 267-270.
Keisuke Tsuzuki et al., "Thermostable Mutants of the Photoprotein Aequorin Obtained by in Vitro Evolution," The Journal of Biological Chemistry, Oct. 7, 2005, vol. 280, No. 40, pp. 34324-34331.
Ludovic Tricoire et al., "Calcium dependence of aequorin bioluminescence dissected by random mutagenesis," Proc. Natl. Acad. Sci., Jun. 20, 2006, vol. 103, No. 25, pp. 9500-9505.
Satoshi Inouye et al., "Application of new semisynthetic aequorins with long half-decay time of luminescence to G-protein-coupled receptor assay," Analytical Biochemistry, 2010, 407, pp. 247-252, including Supplementary data.
Masoume et al., "Site-specific mutagenesis of the calcium-binding photoprotein aequorin at EF hand I", Clinical Biochemistry, Sep. 2011, vol. 44, p. S87.
GB Search Report mailed Aug. 1, 2012 in GB Application No. GB125944.0.

*Primary Examiner* — Chih-Min Kam
(74) *Attorney, Agent, or Firm* — Drinker Biddle & Reath LLP

(57) ABSTRACT

Calcium-binding photoproteins showing the luminescence pattern with a slow decay of are desired. The invention provides a mutant apoprotein comprising an amino acid sequence wherein the 23rd to 34th amino acids in the amino acid sequence of SEQ ID NO: 2 are substituted with an amino acid represented by formula I below: Xaa23-Xaa24-Xaa25-Xaa26-Xaa27-Xaa28-Xaa29-Xaa30-Xaa31-Xaa32-Xaa33-Xaa 34; having a function to bind to the peroxide of coelenterazine or the peroxide of a coelenterazine analogue to form a photoprotein capable of emitting light under the action of calcium ions; and, having a half decay time of the luminescence emitted by binding of the photoprotein to calcium ions being not less than 2 seconds.

13 Claims, 4 Drawing Sheets

(a)

(b)

MKKTAIAIAVALAGFATVAQA ANS HHHHHHG KLTSDFD...GGAVP *
OmpA sequence          histidine tag  mutant aequorin–AM20
                                         (188 a.a.)

SEQUENCE LISTING

<160> NUMBER OF SEQ ID NOS: 89

<210> SEQ ID NO 1
<211> LENGTH: 567
<212> TYPE: DNA
<213> ORGANISM: Aequorea victoria
<220> FEATURE:
<221> NAME/KEY: CDS
<222> LOCATION: (1)..(567)

<400> SEQUENCE: 1

```
aag ctt aca tca gac ttc gac aac cca aga tgg att gga cga cac aag    48
Lys Leu Thr Ser Asp Phe Asp Asn Pro Arg Trp Ile Gly Arg His Lys
1               5                   10                  15 cat atg ttc aat ttt cta gat gtc aac cac aat gga aaa atc tct ctt    96
His Met Phe Asn Phe Leu Asp Val Asn His Asn Gly Lys Ile Ser Leu
            20                  25                  30 gac gag atg gtc tac aag gca tct gat att gtc atc aat aac ctt gga   144
Asp Glu Met Val Tyr Lys Ala Ser Asp Ile Val Ile Asn Asn Leu Gly
        35                  40                  45 gca aca cct gag caa gcc aaa cga cac aaa gat gct gta gaa gcc ttc   192
Ala Thr Pro Glu Gln Ala Lys Arg His Lys Asp Ala Val Glu Ala Phe
    50                  55                  60 ttc gga gga gct gga atg aaa tat ggt gtg gaa act gat tgg cct gca   240
Phe Gly Gly Ala Gly Met Lys Tyr Gly Val Glu Thr Asp Trp Pro Ala
65                  70                  75                  80 tat att gaa gga tgg aaa aaa ttg gct act gat gaa ttg gag aaa tac   288
Tyr Ile Glu Gly Trp Lys Lys Leu Ala Thr Asp Glu Leu Glu Lys Tyr
                85                  90                  95 gcc aaa aac gaa cca acg ctc atc cgt ata tgg ggt gat gct ttg ttt   336
Ala Lys Asn Glu Pro Thr Leu Ile Arg Ile Trp Gly Asp Ala Leu Phe
            100                 105                 110 gat atc gtt gac aaa gat caa aat gga gcc att aca ctg gat gaa tgg   384
Asp Ile Val Asp Lys Asp Gln Asn Gly Ala Ile Thr Leu Asp Glu Trp
        115                 120                 125 aaa gca tac acc aaa gct gct ggt atc atc caa tca tca gaa gat tgc   432
Lys Ala Tyr Thr Lys Ala Ala Gly Ile Ile Gln Ser Ser Glu Asp Cys
    130                 135                 140 gag gaa aca ttc aga gtg tgc gat att gat gaa agt gga caa ctc gat   480
Glu Glu Thr Phe Arg Val Cys Asp Ile Asp Glu Ser Gly Gln Leu Asp
145                 150                 155                 160 gtt gat gag atg aca aga caa cat tta gga ttt tgg tac acc atg gat   528
Val Asp Glu Met Thr Arg Gln His Leu Gly Phe Trp Tyr Thr Met Asp
                165                 170                 175 cct gct tgc gaa aag ctc tac ggt gga gct gtc ccc taa                567
Pro Ala Cys Glu Lys Leu Tyr Gly Gly Ala Val Pro
            180                 185
```

<210> SEQ ID NO 2
<211> LENGTH: 188
<212> TYPE: PRT
<213> ORGANISM: Aequorea victoria

<400> SEQUENCE: 2

```
Lys Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
            20                  25                  30

Asp Glu Met Val Tyr Lys Ala Ser Asp Ile Val Ile Asn Asn Leu Gly
        35                  40                  45
```

```
Ala Thr Pro Glu Gln Ala Lys Arg His Lys Asp Ala Val Glu Ala Phe
    50                  55                  60

Phe Gly Gly Ala Gly Met Lys Tyr Gly Val Glu Thr Asp Trp Pro Ala
 65                  70                  75                  80

Tyr Ile Glu Gly Trp Lys Lys Leu Ala Thr Asp Glu Leu Glu Lys Tyr
                 85                  90                  95

Ala Lys Asn Glu Pro Thr Leu Ile Arg Ile Trp Gly Asp Ala Leu Phe
            100                 105                 110

Asp Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
    130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185

<210> SEQ ID NO 3
<211> LENGTH: 591
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(591)

<400> SEQUENCE: 3 atg acc atg att acg cca agc tgc aag ctt aca tca gac ttc gac aac      48
Met Thr Met Ile Thr Pro Ser Cys Lys Leu Thr Ser Asp Phe Asp Asn
  1               5                  10                  15 cca aga tgg att gga cga cac aag cat atg ttc aat ttt cta gat gtc      96
Pro Arg Trp Ile Gly Arg His Lys His Met Phe Asn Phe Leu Asp Val
             20                  25                  30 aac cac aat gga aaa atc tct ctt gac gag atg gtc tac aag gca tct     144
Asn His Asn Gly Lys Ile Ser Leu Asp Glu Met Val Tyr Lys Ala Ser
         35                  40                  45 gat att gtc atc aat aac ctt gga gca aca cct gag caa gcc aaa cga     192
Asp Ile Val Ile Asn Asn Leu Gly Ala Thr Pro Glu Gln Ala Lys Arg
     50                  55                  60 cac aaa gat gct gta gaa gcc ttc ttc gga gga gct gga atg aaa tat     240
His Lys Asp Ala Val Glu Ala Phe Phe Gly Gly Ala Gly Met Lys Tyr
 65                  70                  75                  80 ggt gtg gaa act gat tgg cct gca tat att gaa gga tgg aaa aaa ttg     288
Gly Val Glu Thr Asp Trp Pro Ala Tyr Ile Glu Gly Trp Lys Lys Leu
                 85                  90                  95 gct act gat gaa ttg gag aaa tac gcc aaa aac gaa cca acg ctc atc     336
Ala Thr Asp Glu Leu Glu Lys Tyr Ala Lys Asn Glu Pro Thr Leu Ile
            100                 105                 110 cgt ata tgg ggt gat gct ttg ttt gat atc gtt gac aaa gat caa aat     384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt     432
Gly Ala Ile Thr Leu Asp Glu Trp Lys Ala Tyr Thr Lys Ala Ala Gly
    130                 135                 140
```

```
atc atc caa tca tca gaa gat tgc gag gaa aca ttc aga gtg tgc gat      480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat      528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt      576
Leu Gly Phe Trp Tyr Thr Met Asp Pro Ala Cys Glu Lys Leu Tyr Gly
            180                 185                 190 gga gct gtc ccc taa                                                  591
Gly Ala Val Pro
        195
```

<210> SEQ ID NO 4
<211> LENGTH: 196
<212> TYPE: PRT
<213> ORGANISM: Artificial sequence
<220> FEATURE:
<223> OTHER INFORMATION: Synthetic Construct

<400> SEQUENCE: 4

```
Met Thr Met Ile Thr Pro Ser Cys Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195
```

<210> SEQ ID NO 5
<211> LENGTH: 564
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(564)

<400> SEQUENCE: 5

```
aag ctt aca tca gac ttc gac aac cca aga tgg att gga cga cac aag      48
Lys Leu Thr Ser Asp Phe Asp Asn Pro Arg Trp Ile Gly Arg His Lys
 1               5                  10                  15 cat atg ttc aat ttt cta gac aaa gat caa aat gga gcc att aca ctg      96
His Met Phe Asn Phe Leu Asp Lys Asp Gln Asn Gly Ala Ile Thr Leu
            20                  25                  30 gat gaa atg gtc tac aag gca tct gat att gtc atc aat aac ctt gga     144
Asp Glu Met Val Tyr Lys Ala Ser Asp Ile Val Ile Asn Asn Leu Gly
        35                  40                  45 gca aca cct gag caa gcc aaa cga cac aaa gat gct gta gaa gcc ttc     192
Ala Thr Pro Glu Gln Ala Lys Arg His Lys Asp Ala Val Glu Ala Phe
    50                  55                  60 ttc gga gga gct gga atg aaa tat ggt gtg gaa act gat tgg cct gca     240
Phe Gly Gly Ala Gly Met Lys Tyr Gly Val Glu Thr Asp Trp Pro Ala
65                  70                  75                  80 tat att gaa gga tgg aaa aaa ttg gct act gat gaa ttg gag aaa tac     288
Tyr Ile Glu Gly Trp Lys Lys Leu Ala Thr Asp Glu Leu Glu Lys Tyr
                85                  90                  95 gcc aaa aac gaa cca acg ctc atc cgt ata tgg ggt gat gct ttg ttt     336
Ala Lys Asn Glu Pro Thr Leu Ile Arg Ile Trp Gly Asp Ala Leu Phe
            100                 105                 110 gat atc gtt gac aaa gat caa aat gga gcc att aca ctg gat gaa tgg     384
Asp Ile Val Asp Lys Asp Gln Asn Gly Ala Ile Thr Leu Asp Glu Trp
        115                 120                 125 aaa gca tac acc aaa gct gct ggt atc atc caa tca tca gaa gat tgc     432
Lys Ala Tyr Thr Lys Ala Ala Gly Ile Ile Gln Ser Ser Glu Asp Cys
    130                 135                 140 gag gaa aca ttc aga gtg tgc gat att gat gaa agt gga caa ctc gat     480
Glu Glu Thr Phe Arg Val Cys Asp Ile Asp Glu Ser Gly Gln Leu Asp
145                 150                 155                 160 gtt gat gag atg aca aga caa cat tta gga ttt tgg tac acc atg gat     528
Val Asp Glu Met Thr Arg Gln His Leu Gly Phe Trp Tyr Thr Met Asp
                165                 170                 175 cct gct tgc gaa aag ctc tac ggt gga gct gtc ccc                     564
Pro Ala Cys Glu Lys Leu Tyr Gly Gly Ala Val Pro
            180                 185
```

<210> SEQ ID NO 6
<211> LENGTH: 188
<212> TYPE: PRT
<213> ORGANISM: Artificial sequence
<220> FEATURE:
<223> OTHER INFORMATION: Synthetic Construct

<400> SEQUENCE: 6

```
Lys Leu Thr Ser Asp Phe Asp Asn Pro Arg Trp Ile Gly Arg His Lys
 1               5                  10                  15

His Met Phe Asn Phe Leu Asp Lys Asp Gln Asn Gly Ala Ile Thr Leu
            20                  25                  30

Asp Glu Met Val Tyr Lys Ala Ser Asp Ile Val Ile Asn Asn Leu Gly
        35                  40                  45

Ala Thr Pro Glu Gln Ala Lys Arg His Lys Asp Ala Val Glu Ala Phe
    50                  55                  60

Phe Gly Gly Ala Gly Met Lys Tyr Gly Val Glu Thr Asp Trp Pro Ala
65                  70                  75                  80

Tyr Ile Glu Gly Trp Lys Lys Leu Ala Thr Asp Glu Leu Glu Lys Tyr
                85                  90                  95
```

```
Ala Lys Asn Glu Pro Thr Leu Ile Arg Ile Trp Gly Asp Ala Leu Phe
            100                 105                 110

Asp Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
    130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185
```

<210> SEQ ID NO 7
<211> LENGTH: 660
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(660)

<400> SEQUENCE: 7

```
atg aaa aag aca gct atc gcg att gca gtg gca ctg gct ggt ttc gct      48
Met Lys Lys Thr Ala Ile Ala Ile Ala Val Ala Leu Ala Gly Phe Ala
1               5                   10                  15 acc gta gcg cag gcc gcg aat ttc cac cat cac cat cac cat ggt aag      96
Thr Val Ala Gln Ala Ala Asn Phe His His His His His His Gly Lys
            20                  25                  30 ctt aca tca gac ttc gac aac cca aga tgg att gga cga cac aag cat     144
Leu Thr Ser Asp Phe Asp Asn Pro Arg Trp Ile Gly Arg His Lys His
        35                  40                  45 atg ttc aat ttt cta gac aaa gat caa aat gga gcc att aca ctg gat     192
Met Phe Asn Phe Leu Asp Lys Asp Gln Asn Gly Ala Ile Thr Leu Asp
    50                  55                  60 gaa atg gtc tac aag gca tct gat att gtc atc aat aac ctt gga gca     240
Glu Met Val Tyr Lys Ala Ser Asp Ile Val Ile Asn Asn Leu Gly Ala
65                  70                  75                  80 aca cct gag caa gcc aaa cga cac aaa gat gct gta gaa gcc ttc ttc     288
Thr Pro Glu Gln Ala Lys Arg His Lys Asp Ala Val Glu Ala Phe Phe
                85                  90                  95 gga gga gct gga atg aaa tat ggt gtg gaa act gat tgg cct gca tat     336
Gly Gly Ala Gly Met Lys Tyr Gly Val Glu Thr Asp Trp Pro Ala Tyr
            100                 105                 110 att gaa gga tgg aaa aaa ttg gct act gat gaa ttg gag aaa tac gcc     384
Ile Glu Gly Trp Lys Lys Leu Ala Thr Asp Glu Leu Glu Lys Tyr Ala
        115                 120                 125 aaa aac gaa cca acg ctc atc cgt ata tgg ggt gat gct ttg ttt gat     432
Lys Asn Glu Pro Thr Leu Ile Arg Ile Trp Gly Asp Ala Leu Phe Asp
    130                 135                 140 atc gtt gac aaa gat caa aat gga gcc att aca ctg gat gaa tgg aaa     480
Ile Val Asp Lys Asp Gln Asn Gly Ala Ile Thr Leu Asp Glu Trp Lys
145                 150                 155                 160 gca tac acc aaa gct gct ggt atc atc caa tca tca gaa gat tgc gag     528
Ala Tyr Thr Lys Ala Ala Gly Ile Ile Gln Ser Ser Glu Asp Cys Glu
                165                 170                 175 gaa aca ttc aga gtg tgc gat att gat gaa agt gga caa ctc gat gtt     576
Glu Thr Phe Arg Val Cys Asp Ile Asp Glu Ser Gly Gln Leu Asp Val
            180                 185                 190
```

```
gat gag atg aca aga caa cat tta gga ttt tgg tac acc atg gat cct      624
Asp Glu Met Thr Arg Gln His Leu Gly Phe Trp Tyr Thr Met Asp Pro
        195                 200                 205 gct tgc gaa aag ctc tac ggt gga gct gtc ccc taa                      660
Ala Cys Glu Lys Leu Tyr Gly Gly Ala Val Pro
    210                 215
```

<210> SEQ ID NO 8
<211> LENGTH: 219
<212> TYPE: PRT
<213> ORGANISM: Artificial sequence
<220> FEATURE:
<223> OTHER INFORMATION: Synthetic Construct

<400> SEQUENCE: 8

```
Met Lys Lys Thr Ala Ile Ala Ile Ala Val Ala Leu Ala Gly Phe Ala
1               5                   10                  15

Thr Val Ala Gln Ala Ala Asn Phe His His His His His His Gly Lys
            20                  25                  30

Leu Thr Ser Asp Phe Asp Asn Pro Arg Trp Ile Gly Arg His Lys His
        35                  40                  45

Met Phe Asn Phe Leu Asp Lys Asp Gln Asn Gly Ala Ile Thr Leu Asp
    50                  55                  60

Glu Met Val Tyr Lys Ala Ser Asp Ile Val Ile Asn Asn Leu Gly Ala
65                  70                  75                  80

Thr Pro Glu Gln Ala Lys Arg His Lys Asp Ala Val Glu Ala Phe Phe
                85                  90                  95

Gly Gly Ala Gly Met Lys Tyr Gly Val Glu Thr Asp Trp Pro Ala Tyr
            100                 105                 110

Ile Glu Gly Trp Lys Lys Leu Ala Thr Asp Glu Leu Glu Lys Tyr Ala
        115                 120                 125

Lys Asn Glu Pro Thr Leu Ile Arg Ile Trp Gly Asp Ala Leu Phe Asp
    130                 135                 140

Ile Val Asp Lys Asp Gln Asn Gly Ala Ile Thr Leu Ser Glu Trp Lys
145                 150                 155                 160

Ala Tyr Thr Lys Ala Ala Gly Ile Ile Gln Ser Ser Glu Asp Cys Glu
                165                 170                 175

Glu Thr Phe Arg Val Cys Asp Ile Asp Glu Ser Gly Gln Leu Asp Val
            180                 185                 190

Asp Glu Met Thr Arg Gln His Leu Gly Phe Trp Tyr Thr Met Asp Pro
        195                 200                 205

Ala Cys Glu Lys Leu Tyr Gly Gly Ala Val Pro
    210                 215
```

<210> SEQ ID NO 9
<211> LENGTH: 24
<212> TYPE: DNA
<213> ORGANISM: Artificial sequence
<220> FEATURE:
<223> OTHER INFORMATION: synthetic DNA

<400> SEQUENCE: 9

```
gagcggataa caatttcaca cagg                                           24
```

<210> SEQ ID NO 10
<211> LENGTH: 27
<212> TYPE: DNA
<213> ORGANISM: Artificial sequence
<220> FEATURE:
<223> OTHER INFORMATION: synthetic DNA -continued

<400> SEQUENCE: 10
ccattgtggt tgacatctag aaaattg                                    27

<210> SEQ ID NO 11
<211> LENGTH: 27
<212> TYPE: DNA
<213> ORGANISM: Artificial sequence
<220> FEATURE:
<223> OTHER INFORMATION: synthetic DNA

<400> SEQUENCE: 11
aagcatatgt tcaattttct agatgtc                                    27

<210> SEQ ID NO 12
<211> LENGTH: 24
<212> TYPE: DNA
<213> ORGANISM: Artificial sequence
<220> FEATURE:
<223> OTHER INFORMATION: synthetic DNA

<400> SEQUENCE: 12
cgccagggtt ttcccagtca cgac                                       24

<210> SEQ ID NO 13
<211> LENGTH: 12
<212> TYPE: PRT
<213> ORGANISM: Aequorea victoria

<400> SEQUENCE: 13

Asp Val Asn His Asn Gly Lys Ile Ser Leu Asp Glu
1               5                   10

<210> SEQ ID NO 14
<211> LENGTH: 12
<212> TYPE: PRT
<213> ORGANISM: Aequorea victoria

<400> SEQUENCE: 14

Asp Lys Asp Gln Asn Gly Ala Ile Thr Leu Asp Glu
1               5                   10

<210> SEQ ID NO 15
<211> LENGTH: 44
<212> TYPE: DNA
<213> ORGANISM: Artificial sequence
<220> FEATURE:
<223> OTHER INFORMATION: synthetic DNA

<400> SEQUENCE: 15
ctagacaaag atcaaaatgg cgccattaca ctggatgaaa tggt                 44

<210> SEQ ID NO 16
<211> LENGTH: 42
<212> TYPE: DNA
<213> ORGANISM: Artificial sequence
<220> FEATURE:
<223> OTHER INFORMATION: synthetic DNA

<400> SEQUENCE: 16
agaccatttc atccagtgta atggcgccat tttgatcttt gt                   42

<210> SEQ ID NO 17
<211> LENGTH: 12
<212> TYPE: PRT

<213> ORGANISM: Aequorea victoria

<400> SEQUENCE: 17

Asp Ile Asp Glu Ser Gly Gln Leu Asp Val Asp Glu
1               5                   10

<210> SEQ ID NO 18
<211> LENGTH: 44
<212> TYPE: DNA
<213> ORGANISM: Artificial sequence
<220> FEATURE:
<223> OTHER INFORMATION: synthetic DNA

<400> SEQUENCE: 18
ctagatatcg atgaaagtgg acaactcgac gtcgatgaga tggt            44

<210> SEQ ID NO 19
<211> LENGTH: 42
<212> TYPE: DNA
<213> ORGANISM: Artificial sequence
<220> FEATURE:
<223> OTHER INFORMATION: synthetic DNA

<400> SEQUENCE: 19
agaccatctc atcgacgtcg agttgtccac tttcatcgat at              42

<210> SEQ ID NO 20
<211> LENGTH: 12
<212> TYPE: PRT
<213> ORGANISM: Clytia gregaria

<400> SEQUENCE: 20

Asp Ile Asn Gly Asp Gly Lys Ile Thr Leu Asp Glu
1               5                   10

<210> SEQ ID NO 21
<211> LENGTH: 44
<212> TYPE: DNA
<213> ORGANISM: Artificial sequence
<220> FEATURE:
<223> OTHER INFORMATION: synthetic DNA

<400> SEQUENCE: 21
ctagacatta atggcgacgg aaaaatcact ttggatgaaa tggt            44

<210> SEQ ID NO 22
<211> LENGTH: 42
<212> TYPE: DNA
<213> ORGANISM: Artificial sequence
<220> FEATURE:
<223> OTHER INFORMATION: synthetic DNA

<400> SEQUENCE: 22
agaccatttc atccaaagtg attttccgt cgccattaat gt               42

<210> SEQ ID NO 23
<211> LENGTH: 12
<212> TYPE: PRT
<213> ORGANISM: Clytia gregaria

<400> SEQUENCE: 23

Asp Lys Asp Gly Ser Gly Ser Ile Ser Leu Asp Glu
1               5                   10

<210> SEQ ID NO 24

<211> LENGTH: 44
<212> TYPE: DNA
<213> ORGANISM: Artificial sequence
<220> FEATURE:
<223> OTHER INFORMATION: synthetic DNA

<400> SEQUENCE: 24
ctagacaaag acggaagtgg ctcgatatca ttggacgaaa tggt       44

<210> SEQ ID NO 25
<211> LENGTH: 42
<212> TYPE: DNA
<213> ORGANISM: Artificial sequence
<220> FEATURE:
<223> OTHER INFORMATION: synthetic DNA

<400> SEQUENCE: 25
agaccatttc gtccaatgat atcgagccac ttccgtcttt gt         42

<210> SEQ ID NO 26
<211> LENGTH: 12
<212> TYPE: PRT
<213> ORGANISM: Clytia gregaria

<400> SEQUENCE: 26

Asp Leu Asp Asn Ser Gly Lys Leu Asp Val Asp Glu
1               5                   10

<210> SEQ ID NO 27
<211> LENGTH: 44
<212> TYPE: DNA
<213> ORGANISM: Artificial sequence
<220> FEATURE:
<223> OTHER INFORMATION: synthetic DNA

<400> SEQUENCE: 27
ctagatttgg acaacagtgg caaacttgat gtcgacgaga tggt       44

<210> SEQ ID NO 28
<211> LENGTH: 42
<212> TYPE: DNA
<213> ORGANISM: Artificial sequence
<220> FEATURE:
<223> OTHER INFORMATION: synthetic DNA

<400> SEQUENCE: 28
agaccatctc gtcgacatca gtttgccac tgttgtccaa at          42

<210> SEQ ID NO 29
<211> LENGTH: 12
<212> TYPE: PRT
<213> ORGANISM: Clytia gregaria

<400> SEQUENCE: 29

Asp Ile Asn Gly Asn Gly Lys Ile Thr Leu Asp Glu
1               5                   10

<210> SEQ ID NO 30
<211> LENGTH: 48
<212> TYPE: DNA
<213> ORGANISM: Artificial sequence
<220> FEATURE:
<223> OTHER INFORMATION: synthetic DNA

<400> SEQUENCE: 30
ctagatatca acggtaatgg gaaaatcaca ttagatgaaa tggtctac   48

<210> SEQ ID NO 31
<211> LENGTH: 42
<212> TYPE: DNA
<213> ORGANISM: Artificial sequence
<220> FEATURE:
<223> OTHER INFORMATION: synthetic DNA

<400> SEQUENCE: 31
agaccatttc atctaatgtg attttcccat taccgttgat at                          42

<210> SEQ ID NO 32
<211> LENGTH: 12
<212> TYPE: PRT
<213> ORGANISM: Clytia gregaria

<400> SEQUENCE: 32

Asp Lys Asp Ala Ser Gly Ser Ile Ser Leu Asp Glu
1               5                   10

<210> SEQ ID NO 33
<211> LENGTH: 48
<212> TYPE: DNA
<213> ORGANISM: Artificial sequence
<220> FEATURE:
<223> OTHER INFORMATION: synthetic DNA

<400> SEQUENCE: 33
ctagacaaag acgcaagtgg ctcgatatct ttagacgaaa tggtctac                    48

<210> SEQ ID NO 34
<211> LENGTH: 42
<212> TYPE: DNA
<213> ORGANISM: Artificial sequence
<220> FEATURE:
<223> OTHER INFORMATION: synthetic DNA

<400> SEQUENCE: 34
agaccatttc gtctaaagat atcgagccac ttgcgtcttt gt                          42

<210> SEQ ID NO 35
<211> LENGTH: 12
<212> TYPE: PRT
<213> ORGANISM: Clytia gregaria

<400> SEQUENCE: 35

Asp Leu Asp Asn Ser Gly Lys Leu Asp Val Asp Glu
1               5                   10

<210> SEQ ID NO 36
<211> LENGTH: 48
<212> TYPE: DNA
<213> ORGANISM: Artificial sequence
<220> FEATURE:
<223> OTHER INFORMATION: synthetic DNA

<400> SEQUENCE: 36
ctagatttgg acaacagtgg caaacttgat gtcgacgaga tggtctac                    48

<210> SEQ ID NO 37
<211> LENGTH: 42
<212> TYPE: DNA
<213> ORGANISM: Artificial sequence
<220> FEATURE:
<223> OTHER INFORMATION: synthetic DNA

<400> SEQUENCE: 37
agaccatctc gtcgacatca agtttgccac tgttgtccaa at        42

<210> SEQ ID NO 38
<211> LENGTH: 12
<212> TYPE: PRT
<213> ORGANISM: Mitrocoma cellularia

<400> SEQUENCE: 38

Asp Ile Asn Ser Asn Gly Gln Ile Asn Leu Asn Glu
1               5                   10

<210> SEQ ID NO 39
<211> LENGTH: 48
<212> TYPE: DNA
<213> ORGANISM: Artificial sequence
<220> FEATURE:
<223> OTHER INFORMATION: synthetic DNA

<400> SEQUENCE: 39
ctagatatca attcaaatgg ccaaatcaat ctgaatgaaa tggtctac        48

<210> SEQ ID NO 40
<211> LENGTH: 42
<212> TYPE: DNA
<213> ORGANISM: Artificial sequence
<220> FEATURE:
<223> OTHER INFORMATION: synthetic DNA

<400> SEQUENCE: 40
agaccatttc attcagattg atttggccat ttgaattgat at        42

<210> SEQ ID NO 41
<211> LENGTH: 12
<212> TYPE: PRT
<213> ORGANISM: Mitrocoma cellularia

<400> SEQUENCE: 41

Asp Lys Asp Arg Asn Gly Ser Val Ser Leu Asp Glu
1               5                   10

<210> SEQ ID NO 42
<211> LENGTH: 48
<212> TYPE: DNA
<213> ORGANISM: Artificial sequence
<220> FEATURE:
<223> OTHER INFORMATION: synthetic DNA

<400> SEQUENCE: 42
ctagacaaag atagaaatgg atccgtttcg ttagacgaaa tggtctac        48

<210> SEQ ID NO 43
<211> LENGTH: 42
<212> TYPE: DNA
<213> ORGANISM: Artificial sequence
<220> FEATURE:
<223> OTHER INFORMATION: synthetic DNA

<400> SEQUENCE: 43
agaccatttc gtctaacgaa acggatccat ttctatcttt gt        42

<210> SEQ ID NO 44
<211> LENGTH: 12
<212> TYPE: PRT
<213> ORGANISM: Mitrocoma cellularia

<400> SEQUENCE: 44

Asp Leu Asp Gly Asp Gly Lys Leu Asp Val Asp Glu
1               5                   10

<210> SEQ ID NO 45
<211> LENGTH: 48
<212> TYPE: DNA
<213> ORGANISM: Artificial sequence
<220> FEATURE:
<223> OTHER INFORMATION: synthetic DNA

<400> SEQUENCE: 45
ctagatttag atggtgacgg taaacttgat gtcgacgaaa tggtctac                    48

<210> SEQ ID NO 46
<211> LENGTH: 42
<212> TYPE: DNA
<213> ORGANISM: Artificial sequence
<220> FEATURE:
<223> OTHER INFORMATION: synthetic DNA

<400> SEQUENCE: 46
agaccatttc gtcgacatca agtttaccgt caccatctaa at                          42

<210> SEQ ID NO 47
<211> LENGTH: 12
<212> TYPE: PRT
<213> ORGANISM: Renilla reniformis

<400> SEQUENCE: 47

Asp Val Thr Gly Asp Gly Phe Ile Ser Arg Glu Asp
1               5                   10

<210> SEQ ID NO 48
<211> LENGTH: 44
<212> TYPE: DNA
<213> ORGANISM: Artificial sequence
<220> FEATURE:
<223> OTHER INFORMATION: synthetic DNA

<400> SEQUENCE: 48
ctagatgtca ccggcgatgg attcatctct cgagaggaca tggt                        44

<210> SEQ ID NO 49
<211> LENGTH: 42
<212> TYPE: DNA
<213> ORGANISM: Artificial sequence
<220> FEATURE:
<223> OTHER INFORMATION: synthetic DNA

<400> SEQUENCE: 49
agaccatgtc ctctcgagag atgaatccat cgccggtgac at                          42

<210> SEQ ID NO 50
<211> LENGTH: 12
<212> TYPE: PRT
<213> ORGANISM: Renilla reniformis

<400> SEQUENCE: 50

Asp Thr Asp Lys Asp Gly Tyr Val Ser Leu Pro Glu
1               5                   10

<210> SEQ ID NO 51
<211> LENGTH: 48

```
<212> TYPE: DNA
<213> ORGANISM: Artificial sequence
<220> FEATURE:
<223> OTHER INFORMATION: synthetic DNA

<400> SEQUENCE: 51
ctagatactg ataaagatgg ttatgtttct ttacccgaga tggtctac                    48

<210> SEQ ID NO 52
<211> LENGTH: 42
<212> TYPE: DNA
<213> ORGANISM: Artificial sequence
<220> FEATURE:
<223> OTHER INFORMATION: synthetic DNA

<400> SEQUENCE: 52
agaccatctc gggtaaagaa acataaccat ctttatcagt at                          42

<210> SEQ ID NO 53
<211> LENGTH: 12
<212> TYPE: PRT
<213> ORGANISM: Renilla reniformis

<400> SEQUENCE: 53

Asp Phe Asn Lys Asn Gly Gln Ile Ser Arg Asp Glu
1               5                   10

<210> SEQ ID NO 54
<211> LENGTH: 48
<212> TYPE: DNA
<213> ORGANISM: Artificial sequence
<220> FEATURE:
<223> OTHER INFORMATION: synthetic DNA

<400> SEQUENCE: 54
ctagatttta ataaaaatgg ccagatatct cgtgatgaga tggtctac                    48

<210> SEQ ID NO 55
<211> LENGTH: 42
<212> TYPE: DNA
<213> ORGANISM: Artificial sequence
<220> FEATURE:
<223> OTHER INFORMATION: synthetic DNA

<400> SEQUENCE: 55
agaccatctc atcacgagat atctggccat ttttattaaa at                          42

<210> SEQ ID NO 56
<211> LENGTH: 12
<212> TYPE: PRT
<213> ORGANISM: Artificial sequence
<220> FEATURE:
<223> OTHER INFORMATION: Synthetic Construct

<400> SEQUENCE: 56

Asp Lys Asp Gly Asp Gly Thr Ile Thr Thr Lys Glu
1               5                   10

<210> SEQ ID NO 57
<211> LENGTH: 44
<212> TYPE: DNA
<213> ORGANISM: Artificial sequence
<220> FEATURE:
<223> OTHER INFORMATION: synthetic DNA

<400> SEQUENCE: 57
```
ctagataaag acggcgatgg caccatcaca acaaaggaaa tggt				44

<210> SEQ ID NO 58
<211> LENGTH: 42
<212> TYPE: DNA
<213> ORGANISM: Artificial sequence
<220> FEATURE:
<223> OTHER INFORMATION: synthetic DNA

<400> SEQUENCE: 58
agaccatttc ctttgttgtg atggtgccat cgccgtcttt at				42

<210> SEQ ID NO 59
<211> LENGTH: 12
<212> TYPE: PRT
<213> ORGANISM: Artificial sequence
<220> FEATURE:
<223> OTHER INFORMATION: Synthetic Construct

<400> SEQUENCE: 59

Asp Ala Asp Gly Asn Gly Thr Ile Asp Phe Pro Glu
1               5                   10

<210> SEQ ID NO 60
<211> LENGTH: 44
<212> TYPE: DNA
<213> ORGANISM: Artificial sequence
<220> FEATURE:
<223> OTHER INFORMATION: synthetic DNA

<400> SEQUENCE: 60
ctagacgctg atggtaatgg taccattgac ttcccagaaa tggt				44

<210> SEQ ID NO 61
<211> LENGTH: 42
<212> TYPE: DNA
<213> ORGANISM: Artificial sequence
<220> FEATURE:
<223> OTHER INFORMATION: synthetic DNA

<400> SEQUENCE: 61
agaccatttc tgggaagtca atggtaccat taccatcagc gt				42

<210> SEQ ID NO 62
<211> LENGTH: 12
<212> TYPE: PRT
<213> ORGANISM: Artificial sequence
<220> FEATURE:
<223> OTHER INFORMATION: Synthetic Construct

<400> SEQUENCE: 62

Asp Lys Asp Gly Asn Gly Tyr Ile Ser Ala Ala Glu
1               5                   10

<210> SEQ ID NO 63
<211> LENGTH: 44
<212> TYPE: DNA
<213> ORGANISM: Artificial sequence
<220> FEATURE:
<223> OTHER INFORMATION: synthetic DNA

<400> SEQUENCE: 63
ctagataagg atggcaatgg ctatatcagt gctgcagaaa tggt				44

<210> SEQ ID NO 64
<211> LENGTH: 42

<210> SEQ ID NO 64
<211> LENGTH: 42
<212> TYPE: DNA
<213> ORGANISM: Artificial sequence
<220> FEATURE:
<223> OTHER INFORMATION: synthetic DNA

<400> SEQUENCE: 64
agaccatttc tgcagcactg atatagccat tgccatcctt at                                    42

<210> SEQ ID NO 65
<211> LENGTH: 12
<212> TYPE: PRT
<213> ORGANISM: Artificial sequence
<220> FEATURE:
<223> OTHER INFORMATION: Synthetic Construct

<400> SEQUENCE: 65

Asp Ile Asp Gly Asp Gly Gln Val Asn Tyr Glu Glu
1               5                   10

<210> SEQ ID NO 66
<211> LENGTH: 44
<212> TYPE: DNA
<213> ORGANISM: Artificial sequence
<220> FEATURE:
<223> OTHER INFORMATION: synthetic DNA

<400> SEQUENCE: 66
ctagatatcg atggagatgg ccaagttaac tacgaagaaa tggt                                  44

<210> SEQ ID NO 67
<211> LENGTH: 42
<212> TYPE: DNA
<213> ORGANISM: Artificial sequence
<220> FEATURE:
<223> OTHER INFORMATION: synthetic DNA

<400> SEQUENCE: 67
agaccatttc ttcgtagtta acttggccat ctccatcgat at                                    42

<210> SEQ ID NO 68
<211> LENGTH: 12
<212> TYPE: PRT
<213> ORGANISM: Artificial sequence
<220> FEATURE:
<223> OTHER INFORMATION: Synthetic Construct

<400> SEQUENCE: 68

Asp Phe Asp Lys Asp Gly Ala Ile Thr Arg Met Asp
1               5                   10

<210> SEQ ID NO 69
<211> LENGTH: 44
<212> TYPE: DNA
<213> ORGANISM: Artificial sequence
<220> FEATURE:
<223> OTHER INFORMATION: synthetic DNA

<400> SEQUENCE: 69
ctagatttcg acaaggatgg agccatcacg cgtatggaca tggt                                  44

<210> SEQ ID NO 70
<211> LENGTH: 42
<212> TYPE: DNA
<213> ORGANISM: Artificial sequence
<220> FEATURE:
<223> OTHER INFORMATION: synthetic DNA

<400> SEQUENCE: 70
agaccatgtc catacgcgtg atggctccat ccttgtcgaa at                    42

<210> SEQ ID NO 71
<211> LENGTH: 12
<212> TYPE: PRT
<213> ORGANISM: Artificial sequence
<220> FEATURE:
<223> OTHER INFORMATION: Synthetic Construct

<400> SEQUENCE: 71

Asp Lys Asn His Asn Gly Ala Ile Ser Leu Asp Glu
1               5                   10

<210> SEQ ID NO 72
<211> LENGTH: 44
<212> TYPE: DNA
<213> ORGANISM: Artificial sequence
<220> FEATURE:
<223> OTHER INFORMATION: synthetic DNA

<400> SEQUENCE: 72
ctagataaaa accacaatgg agcgatatct cttgacgaga tggt                  44

<210> SEQ ID NO 73
<211> LENGTH: 42
<212> TYPE: DNA
<213> ORGANISM: Artificial sequence
<220> FEATURE:
<223> OTHER INFORMATION: synthetic DNA

<400> SEQUENCE: 73
agaccatctc gtcaagagat atcgctccat tgtggttttt at                    42

<210> SEQ ID NO 74
<211> LENGTH: 12
<212> TYPE: PRT
<213> ORGANISM: Artificial sequence
<220> FEATURE:
<223> OTHER INFORMATION: Synthetic Construct

<400> SEQUENCE: 74

Asp Arg Asn His Asn Gly Lys Ile Ser Leu Asp Glu
1               5                   10

<210> SEQ ID NO 75
<211> LENGTH: 44
<212> TYPE: DNA
<213> ORGANISM: Artificial sequence
<220> FEATURE:
<223> OTHER INFORMATION: synthetic DNA

<400> SEQUENCE: 75
ctagatcgca accacaatgg aaagatatct cttgacgaga tggt                  44

<210> SEQ ID NO 76
<211> LENGTH: 42
<212> TYPE: DNA
<213> ORGANISM: Artificial sequence
<220> FEATURE:
<223> OTHER INFORMATION: synthetic DNA

<400> SEQUENCE: 76
agaccatctc gtcaagagat atctttccat tgtggttgcg at                    42

```
<210> SEQ ID NO 77
<211> LENGTH: 12
<212> TYPE: PRT
<213> ORGANISM: Artificial sequence
<220> FEATURE:
<223> OTHER INFORMATION: Synthetic Construct

<400> SEQUENCE: 77

Asp Val Asn His Asn Gly Ala Ile Ser Leu Asp Glu
1               5                   10

<210> SEQ ID NO 78
<211> LENGTH: 44
<212> TYPE: DNA
<213> ORGANISM: Artificial sequence
<220> FEATURE:
<223> OTHER INFORMATION: synthetic DNA

<400> SEQUENCE: 78
ctagatgtca accacaatgg agcgatatct cttgacgaga tggt            44

<210> SEQ ID NO 79
<211> LENGTH: 42
<212> TYPE: DNA
<213> ORGANISM: Artificial sequence
<220> FEATURE:
<223> OTHER INFORMATION: synthetic DNA

<400> SEQUENCE: 79
agaccatctc gtcaagagat atcgctccat tgtggttgac at              42

<210> SEQ ID NO 80
<211> LENGTH: 12
<212> TYPE: PRT
<213> ORGANISM: Artificial sequence
<220> FEATURE:
<223> OTHER INFORMATION: Synthetic Construct

<400> SEQUENCE: 80

Asp Arg Asn His Asn Gly Ala Ile Ser Leu Asp Glu
1               5                   10

<210> SEQ ID NO 81
<211> LENGTH: 44
<212> TYPE: DNA
<213> ORGANISM: Artificial sequence
<220> FEATURE:
<223> OTHER INFORMATION: synthetic DNA

<400> SEQUENCE: 81
ctagatcgca accacaatgg agcgatatct cttgacgaga tggt            44

<210> SEQ ID NO 82
<211> LENGTH: 42
<212> TYPE: DNA
<213> ORGANISM: Artificial sequence
<220> FEATURE:
<223> OTHER INFORMATION: synthetic DNA

<400> SEQUENCE: 82
agaccatctc gtcaagagat atcgctccat tgtggttgcg at              42

<210> SEQ ID NO 83
<211> LENGTH: 12
<212> TYPE: PRT
<213> ORGANISM: Aequorea victoria
```

<400> SEQUENCE: 83

Asp Lys Asn His Asn Gly Lys Ile Ser Leu Asp Glu
1               5                   10

<210> SEQ ID NO 84
<211> LENGTH: 44
<212> TYPE: DNA
<213> ORGANISM: Artificial sequence
<220> FEATURE:
<223> OTHER INFORMATION: synthetic DNA

<400> SEQUENCE: 84
ctagataaaa accacaatgg aaagatatct cttgacgaga tggt        44

<210> SEQ ID NO 85
<211> LENGTH: 42
<212> TYPE: DNA
<213> ORGANISM: Artificial sequence
<220> FEATURE:
<223> OTHER INFORMATION: synthetic DNA

<400> SEQUENCE: 85
agaccatctc gtcaagagat atctttccat tgtggttttt at          42

<210> SEQ ID NO 86
<211> LENGTH: 28
<212> TYPE: DNA
<213> ORGANISM: Artificial sequence
<220> FEATURE:
<223> OTHER INFORMATION: synthetic DNA

<400> SEQUENCE: 86
aatttccacc atcaccatca ccatggta                          28

<210> SEQ ID NO 87
<211> LENGTH: 28
<212> TYPE: DNA
<213> ORGANISM: Artificial sequence
<220> FEATURE:
<223> OTHER INFORMATION: synthetic DNA

<400> SEQUENCE: 87
agcttaccat ggtgatggtg atggtgga                          28

<210> SEQ ID NO 88
<211> LENGTH: 60
<212> TYPE: DNA
<213> ORGANISM: Artificial sequence
<220> FEATURE:
<223> OTHER INFORMATION: synthetic DNA

<400> SEQUENCE: 88
agcttcatat ggagctcggt accctcgagg gatccgaatt cgtcgacctg cagtctagag    60

<210> SEQ ID NO 89
<211> LENGTH: 60
<212> TYPE: DNA
<213> ORGANISM: Artificial sequence
<220> FEATURE:
<223> OTHER INFORMATION: synthetic DNA

<400> SEQUENCE: 89
gatcctctag actgcaggtc gacgaattcg gatccctcga gggtaccgag ctccatatga    60

MUTANT APOPROTEIN OF PHOTOPROTEIN WITH LOW CALCIUM SENSITIVITY

The priority application, Japanese patent application no. 2011-083968, filed on Apr. 5, 2011, is incorporated by reference herein in its entirety.

REFERENCE TO A SEQUENCE LISTING

A Sequence Listing containing SEQ ID NO: 1-89 is incorporated herein by reference.

TECHNICAL FIELD

The present invention relates to a novel calcium-binding photoprotein, a gene encoding the same, use thereof, and so on.

BACKGROUND ART

The calcium-binding photoprotein is present as a complex of an apoprotein and the peroxide of coelenterazine as a light-emitting substrate. The calcium-binding photoprotein emits light when the protein binds calcium ions. Among the calcium-binding photoproteins, aequorin, obelin, clytin, mitrocomin, mineopsin. bervoin, etc. are well-characterized.

Aequorin is a representative protein in the calcium-binding photoproteins, and its protein structure and the luminescence mechanism, etc. have been reported in detail (cf., e.g., Inouye et al. (1985) Proc. Natl. Acad. Sci. USA 82, 3154-3158; Head et al. (2000) Nature 405, 372-376; etc.). The homology of the primary structures among the calcium-binding photoproteins is very high, and the luminescence mechanism and protein structure are found to be essentially the same, based on the analysis of the crystal structures of aequorin (PDB: 1EJ3), obelin (PDB: 1EL4, 1JF0, 1QV0) and clytin (PDB: 3KPX). Also, aequorin has an extremely high sensitivity to calcium ions and is used for the detection and quantification of a trace amount of calcium ions, assay for intracellular calcium ion changes, etc.

On the other hand, it is known that the calcium-binding domains in photoproteins have a unique structure, generally termed EF hand structure, which is present in many calcium-binding proteins. That is, the calcium-binding domains in photoproteins have a loop structure which is consisted of alpha helix-loop-alpha helix, and 12 amino acid sequence in the loop structure contains the following consensus sequence: O—O—OGly-Ile(Leu)-O—O (O: oxygen atom-containing amino acid, -: any amino acid). Until now, many aequorin mutants have been constructed by site-directed mutagenesis and random mutagenesis and luminescence activities or luminescence patterns of the aequorin mutants have been analyzed (Tsuji et al (1986) Proc. Natl. Acad. Sci. 83, 8107-8111; Kurose et al. (1989) Proc. Natl. Acad. Sci. 86, 80-84; Kendall et al. (1992) Biochem. Biophys. Res. Commun. 187, 1091-1097; Ohmiya et al (1992) FEBS Lett. 301, 197-201; Ohmiya et al (1993) FEBS Lett. 320, 267-270; Tsuzuki et al. (2005) J. Biol. Chem. 280, 34324-34331; Tricoire et al. (2006) Proc. Natl. Acad. Sci. 103, 9500-9505; etc.).

Among these photoproteins, it has been reported that some photoproteins show a rapid decay pattern of luminescence and some photoproteins show a slow decay pattern of luminescence by adding calcium. All of the aequorin mutants showing a slow decay pattern of luminescence that have been reported so far are obtained by substitution of amino acids containing oxygen atoms in the loop region of the EF hand structure (Kendall et al. (1992) Biochem. Biophys. Res. Commun. 187, 1091-1097; Tsuzuki et al. (2005) J. Biol. Chem. 280, 34324-34331; Tricoire et al. (2006) Proc. Natl. Acad. Sci. 103, 9500-9505; etc.).

Aequorin has been widely used in the dynamic analysis of intracellular calcium ions for screening the target compound for G protein-coupled receptors in drug development. In recent years, much attention has been focused on a method for screening a target compound using semisynthetic aequorins showing a slow decay pattern of luminescence, namely, with less sensitivity to calcium, and a screening method using analogues of coelenterazine as a light-emitting substrate has been established (Inouye et al. (2010) Anal. Biochem. 407, 247-252; etc.).

On the other hand, there is also desired an aequorin with low calcium sensitivity in which a decay of the luminescence can be slowed down even when native coelenterazine or h-coelenterazine is used as a light-emitting substrate.

DISCLOSURE OF INVENTION

Under the foregoing circumstances, there are desired a calcium-binding photoprotein showing the luminescence pattern with a slow decay, and the like.

In preparing photoproteins with low calcium sensitivity, the present inventors have paid attention to the calcium-binding domains of aequorin. The loop sequence in calcium-binding domain I of aequorin composed of 12 amino acids is replaced by a loop sequence of the calcium-binding domains from other photoproteins or other calcium-binding proteins to prepare aequorin mutants. By selecting the mutant with a slow decay of the luminescence pattern from the aequorin mutants prepared, a photoprotein with low calcium sensitivity was newly produced. Based on the result, further investigations have been made to accomplish the present invention.

Therefore, the present invention provides a mutant apoprotein of photoprotein having low calcium sensitivity, a polynucleotide, a recombinant vector, a transformant, and so on.

[1] A mutant apoprotein comprising an amino acid sequence in which the 23rd to 34th amino acids in the amino acid sequence of SEQ ID NO: 2 are substituted with an amino acid represented by formula I below: Xaa23-Xaa24-Xaa25-Xaa26-Xaa27-Xaa28-Xaa29-Xaa30-Xaa31-Xaa32-Xaa33-Xaa 34
(wherein:
  Xaa23 is Asp, Glu, Gln, Ser, Thr or Asn,
  Xaa24 is Lys, Arg, His, Leu or Thr,
  Xaa25 is Asp, Glu, Gln, Ser, Thr or Asn,
  Xaa26 is an optional amino acid,
  Xaa27 is Asp, Glu, Gln, Ser, Thr or Asn,
  Xaa28 is Gly,
  Xaa29 is an optional amino acid,
  Xaa30 is Ile, Leu or Val,
  Xaa31 is Asp, Glu, Gln, Ser, Thr or Asn,
  Xaa32 is an optional amino acid,
  Xaa33 is an optional amino acid, and,
  Xaa34 is Asp, Glu, Gln, Ser, Thr or Asn);
having a function to bind to the peroxide of coelenterazine or the peroxide of a coelenterazine analogue to form a photoprotein capable of emitting light under the action of calcium ions; and,
having a half decay time of the luminescence emitted by binding of the photoprotein to calcium ions being not less than 2 seconds.

[2] The mutant apoprotein according to [1] above, wherein in formula I above:
  Xaa23 is Asp,
  Xaa24 is Lys, Arg, Leu or Thr, Xaa25 is Asn or Asp,
Xaa26 is His, Gln, Asn, Gly, Arg or Lys,
Xaa27 is Asn, Asp or Ser,
Xaa28 is Gly,
Xaa29 is Ala, Lys, Ser or Tyr,
Xaa30 is Ile, Leu or Val,
Xaa31 is Ser, Thr or Asp,
Xaa32 is Leu, Val or Ala,
Xaa33 is Asp, Pro or Ala, and,
Xaa34 is Glu.

[3] The mutant apoprotein according to [2] above, wherein in formula I above:
Xaa23 is Asp,
Xaa24 is Lys,
Xaa25 is Asp,
Xaa26 is Gln,
Xaa27 is Asn,
Xaa28 is Gly,
Xaa29 is Ala,
Xaa30 is Ile,
Xaa31 is Thr,
Xaa32 is Leu,
Xaa33 is Asp, and,
Xaa34 is Glu.

[4] The mutant apoprotein according to [2] above, wherein in formula I above:
Xaa23 is Asp,
Xaa24 is Lys or Arg,
Xaa25 is Asn,
Xaa26 is His,
Xaa27 is Asn,
Xaa28 is Gly,
Xaa29 is Ala or Lys,
Xaa30 is Ile,
Xaa31 is Ser,
Xaa32 is Leu,
Xaa33 is Asp, and,
Xaa34 is Glu.

[5] The mutant apoprotein according to any one of [1] to [4] above, which further contains a secretory signal peptide and/or a peptide for purification.

[6] A mutant apoprotein comprising the amino acid sequence of SEQ ID NO: 8.

[7] A photoprotein consisting of the mutant apoprotein according to any one of [1] to [6] above and the peroxide of coelenterazine or the peroxide of a coelenterazine analogue.

[8] The photoprotein according to [7] above, wherein the coelenterazine analogue is n-coelenterazine, cf3-coelenterazine, i-coelenterazine, meo-coelenterazine or me-coelenterazine.

[9] A polynucleotide comprising a polynucleotide encoding the mutant apoprotein according to any one of [1] to [6] above.

[10] A recombinant vector comprising the polynucleotide according to [9] above.

[11] A transformant transformed with the recombinant vector according to [10] above.

[12] A method for producing the mutant apoprotein according to any one of [1] to [6] above, which comprises the step of culturing the transformant of [11] above to form the mutant apoprotein according to any one of [1] to [6] above.

[13] A kit comprising the mutant apoprotein according to any one of [1] to [6] above or the photoprotein according to [7] or [8] above.

[14] A kit comprising the polynucleotide according to [9] above, the recombinant vector according to [10] above or the transformant according to [11] above.

[15] A method for detecting or determining calcium ions, which comprises using the mutant apoprotein according to any one of [1] to [6] above or the photoprotein according to [7] or [8] above.

[16] A method for measuring the activity of a sequence involved in promoter regulation, which comprises using the polynucleotide according to [9] above as a reporter gene.

[17] A method for measuring changes in intracellular calcium levels, which comprises the step of expressing the polynucleotide according to [9] above to form a photoprotein.

[18] A method for producing a fluorescent protein which comprises reacting the protein according to any one of [1] to [6] above with coelenteramide or its analogue in the presence or absence of a calcium ion or a divalent or trivalent ion replaceable for the calcium ion.

[19] The method according to [18] above, wherein the reaction is performed in the presence of a reducing agent.

[20] The method according to [18] or [19] above, wherein the reaction is performed in the presence of a chelating agent for removing the calcium ion or the divalent or trivalent ion replaceable for the calcium ion.

[21] A method for screening a mutant apoprotein capable of forming a calcium-binding photoprotein with low calcium sensitivity, which comprises:
(1) the step of constructing a mutant apoprotein wherein the loop of EF hand in calcium-binding domain I of apoaequorin is replaced by:
 (a) the loop of EF hand in calcium-binding domain III or IV of apoaequorin, or,
 (b) the loop of any one of EF hands in calcium-binding domains of a calcium-binding protein, which is different from apoaequorin;
(2) the step of determining a half decay time of the luminescence from the calcium-binding photoprotein formed by the mutant apoprotein; and,
(3) the step of selecting a mutant apoprotein of a calcium-binding photoprotein as the mutant apoprotein capable of forming the calcium-binding photoprotein with low calcium sensitivity when the half decay time of the luminescence from the calcium-binding photoprotein is not less than 2 seconds.

The mutant apoprotein of the present invention has the ability to bind to the peroxide of coelenterazine or the peroxide of a coelenterazine analogue and form a photoprotein which emits light under the action of calcium ions. The photoprotein formed from the protein in some embodiment of the present invention can provide a slow decay of luminescence.

BEST MODE FOR CARRYING OUT THE INVENTION

Figure 1:
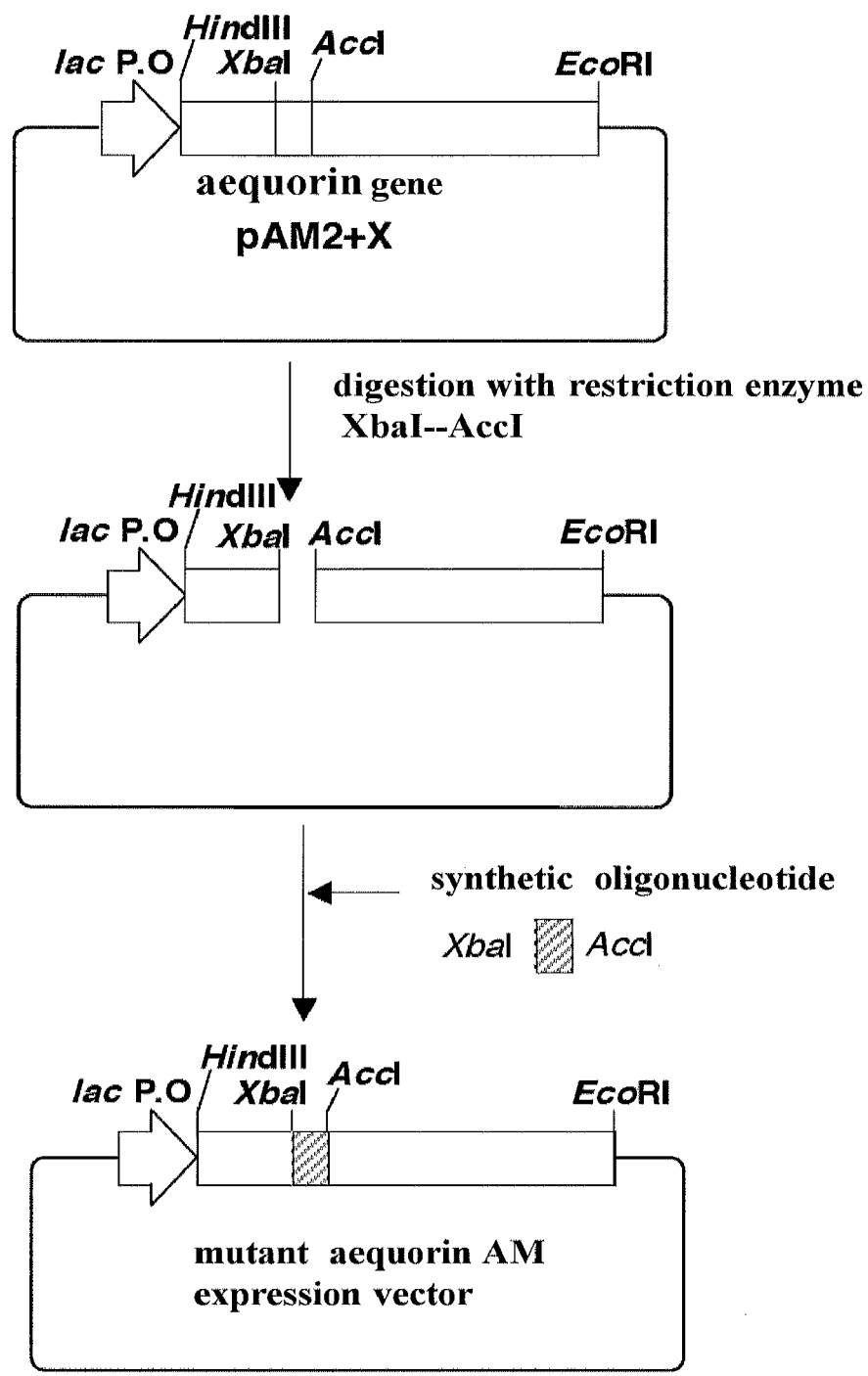
FIG. 1 is a schematic representation showing the construction of expression vectors of mutant apoprotein AM in which the loop sequence in the first calcium-binding site of aequorin (hereinafter sometimes referred to as aequorin EF hand loop [I]) is replaced by the loop sequence of other calcium-binding proteins.

Hereinafter the present invention is described in detail.

1. Mutant Apoprotein of the Invention

The mutant apoprotein of the present invention refers to a mutant apoprotein comprising an amino acid sequence wherein the 23rd to 34th amino acids in the amino acid sequence of SEQ ID NO: 2 are substituted with the following formula I: Xaa23-Xaa24-Xaa25-Xaa26-Xaa27-Xaa28-Xaa29-Xaa30-Xaa31-Xaa32-Xaa33-Xaa 34
(wherein:
  Xaa23 is Asp, Glu, Gln, Ser, Thr or Asn,
  Xaa24 is Lys, Arg, His, Leu or Thr,
  Xaa25 is Asp, Glu, Gln, Ser, Thr or Asn,
  Xaa26 is an optional amino acid,
  Xaa27 is Asp, Glu, Gln, Ser, Thr or Asn,
  Xaa28 is Gly,
  Xaa29 is an optional amino acid,
  Xaa30 is Ile, Leu or Val,
  Xaa31 is Asp, Glu, Gln, Ser, Thr or Asn,
  Xaa32 is an optional amino acid,
  Xaa33 is an optional amino acid, and,
  Xaa34 is Asp, Glu, Gln, Ser, Thr or Asn);
having a function to bind to the peroxide of coelenterazine or the peroxide of a coelenterazine analogue to form a photoprotein capable of emitting light under the action of calcium ions; and,
having a half decay time of the luminescence emitted by binding of the photoprotein to calcium ions being not less than 2 seconds.

The term "to bind to the peroxide of coelenterazine or the peroxide of a coelenterazine analogue to form a photoprotein" is used to mean not only (a) that the mutant apoprotein of the present invention binds to the peroxide of coelenterazine or the peroxide of a coelenterazine analogue to form a photoprotein, but also (b) that the mutant apoprotein of the present invention is brought in contact with coelenterazine or its analogue in the presence of oxygen to form a photoprotein (complex) containing the mutant apoprotein of the present invention and the peroxide of coelenterazine or the peroxide of the coelenterazine analogue.

The photoprotein comprising the mutant apoprotein of the present invention and the peroxide of coelenterazine or the peroxide of a coelenterazine analogue (hereinafter sometimes referred to as "the photoprotein of the present invention") emits light by the action of calcium ions, which can be confirmed by measuring the luminescence activity and luminescence pattern of the photoprotein of the invention according to the methods described in, e.g., Shimomura O. et al. (1988) Biochem. J. 251, 405-410, Shimomura O. et al. Biochem. J. (1989) 261, 913-920, Inouye et al. (2010) Anal. Biochem. 407, 247-252, etc. Specifically, the luminescence activity and luminescence pattern are measured as follows; for example, a calcium solution is added to the photoprotein of the present invention to initiate a luminescence reaction and the luminescence activity and luminescence pattern are measured using a luminometer. Commercially available luminometers, e.g., Centro LB 960 (manufactured by Berthold, Inc.) may be used as the luminometer. The method for measurement of the luminescence activity and luminescence pattern is described in EXAMPLES later given in more details.

The half decay time of luminescence generated by the photoprotein of the present invention bound to calcium ions is longer than that of native aequorin, which can be confirmed by measuring the luminescence activity and luminescence patterns of the photoprotein of the present invention and native aequorin in accordance with the method described above, determining a time period in which the luminescence of the photoprotein of the present invention becomes half of the maximum luminescence intensity (half decay time) and the half decay time of native aequorin from the measured luminescence activity and luminescence patterns, and comparing the half decay time of the two. Native aequorin is a protein expressed with, e.g., expression vector pAM2+X in EXAMPLES described later.

The half decay time of luminescence of the photoprotein in the present invention is longer when compared to native aequorin and is, for example, 2 seconds or longer. Preferably, the half decay time of luminescence of the photoprotein of the present invention is 2.1 seconds or longer, 2.2 seconds or longer, 2.3 seconds or longer, 2.4 seconds or longer, 2.5 seconds or longer, 2.6 seconds or longer, 2.7 seconds or longer, 2.8 seconds or longer, 2.9 seconds or longer, 3.0 seconds or longer, 3.1 seconds or longer, 3.2 seconds or longer, 3.3 seconds or longer, 3.4 seconds or longer, 3.5 seconds or longer, 3.6 seconds or longer, 3.7 seconds or longer, 3.8 seconds or longer, 3.9 seconds or longer, 4.0 seconds or longer, or 4.1 seconds or longer. More preferably, the half decay time of luminescence of the photoprotein of the present invention is more than each of these values and 100 seconds or shorter, 70 seconds or shorter, 50 seconds or shorter, 40 seconds or shorter, 30 seconds or shorter, 29 seconds or shorter, 28 seconds or shorter, 27 seconds or shorter, 26 seconds or shorter, 25 seconds or shorter, 24 seconds or shorter, 23 seconds or shorter, 22 seconds or shorter, or 21.9 seconds or shorter.

The coelenterazine analogue means a compound that can bind to the apoprotein of the present invention to form a photoprotein capable of emitting light by the action of calcium ions. Specific examples of the coelenterazine analogue are given hereinafter.

Specific examples of the amino acid sequences wherein the 23rd to 34th amino acids in the amino acid sequence of SEQ ID NO: 2 are substituted, respectively, with an amino acid represented by formula I: Xaa23-Xaa24-Xaa25-Xaa26-Xaa27-Xaa28-Xaa29-Xaa30-Xaa31-Xaa32-Xaa33-Xaa 34 include an amino acid sequence wherein the 23rd amino acid is substituted with the amino acid residue Xaa23, and in this order, the 24th amino acid with the amino acid residue Xaa24, the 25th amino acid with the amino acid residue Xaa25, the 26th amino acid with the amino acid residue Xaa26, the 27th amino acid with the amino acid residue Xaa27, the 28th amino acid with the amino acid residue Xaa28, the 25th amino acid with the amino acid residue Xaa29, the 30th amino acid with the amino acid residue Xaa30, the 31st amino acid with the amino acid residue Xaa31, the 32nd amino acid with the amino acid residue Xaa32, the 33rd amino acid with the amino acid residue Xaa33, and the 34th amino acid with the amino acid residue Xaa34 in the amino acid sequence of SEQ ID NO: 2.

In formula I, Xaa23 is Asp, Glu, Gln, Ser, Thr or Asn, preferably, Asp, Glu or Gln, and more preferably, Asp.

Xaa24 is Lys, Arg, His, Leu or Thr, preferably, Lys, Arg, Leu or Thr, and more preferably, Lys. In another more preferred embodiment of the present invention, Xaa24 is Lys or Arg.

Xaa25 is Asp, Glu, Gln, Ser, Thr or Asn, preferably, Asp or Asn, and more preferably, Asp. In another more preferred embodiment of the present invention, Xaa25 is Asn.

Xaa26 is an optional amino acid. As used herein, the term "optional amino acid" specifically means Ala, Cys, Asp, Glu, Phe, Gly, His, Ile, Lys, Leu, Met, Asn, Pro, Glu, Arg, Ser, Thr, Val, Trp or Tyr. Xaa26 is preferably His, Gln, Asn, Gly, Arg or Lys, and more preferably, Gln. In another more preferred embodiment of the present invention, Xaa26 is His.

Xaa27 is Asp, Glu, Gln, Ser, Thr or Asn, preferably, Asn, Asp or Ser, and more preferably, Asn.

Xaa28 is Gly.

Xaa29 is an optional amino acid. As used herein, the term "optional amino acid" specifically means the same as given above. Xaa29 is preferably Ala, Lys, Ser or Tyr, and more preferably, Ala. In another more preferred embodiment of the present invention, Xaa29 is Ala or Lys.

Xaa30 is Ile, Leu or Val, and preferably, Ile.

Xaa31 is Asp, Glu, Gln, Ser, Thr or Asn, preferably, Ser, Thr or Asp, and more preferably, Thr. In another more preferred embodiment of the present invention, Xaa31 is Ser.

Xaa32 is an optional amino acid. As used herein, the term "optional amino acid" specifically means the same as given above. Xaa32 is preferably Leu, Val or Ala, and more preferably, Leu.

Xaa33 is an optional amino acid. As used herein, the term "optional amino acid" specifically means the same as given above. Xaa33 is preferably, Asp, Pro or Ala, and more preferably, Asp.

Xaa34 is Asp, Glu, Gln, Ser, Thr or Asn, and preferably, Glu.

In an embodiment of the present invention, Xaa23 is Asp, Xaa24 is Lys, Xaa25 is Asp, Xaa26 is Gln, Xaa27 is Asn, Xaa28 is Gly, Xaa29 is Ala, Xaa30 is Ile, Xaa31 is Thr, Xaa32 is Leu, Xaa33 is Asp and Xaa34 is Glu, in formula I. The amino acid sequence of formula I is shown in SEQ ID NO: 14.

In some other embodiments of the present invention, Xaa23 is Asp, Xaa24 is Lys or Arg, Xaa25 is Asn, Xaa26 is His, Xaa27 is Asn, Xaa28 is Gly, Xaa29 is Ala or Lys, Xaa30 is Ile, Xaa31 is Ser, Xaa32 is Leu, Xaa33 is Asp and Xaa34 is Glu, in formula I. Preferably, the amino acid sequence of formula I is the amino acid sequence of SEQ ID NO: 71, 74, 80 or 83.

In still some other embodiments of the present invention, the amino acid sequence of formula I is the amino acid sequence of SEQ ID NO: 23, 26, 32, 41, 50 or 62.

The mutant apoprotein of the present invention is a protein comprising, e.g., the amino acid sequence of SEQ ID NO: 6.

The mutant apoprotein of the present invention may further contain an additional peptide sequences at the N terminus and/or C terminus, preferably at the N terminus. Examples of the additional peptide sequences include at least one peptide sequence selected from the group consisting of a peptide sequence for purification, a secretory signal peptide sequence and an epitope sequence capable of recognizing an antibody. Preferably, the additional peptide sequence is a peptide sequence for purification and/or a secretory signal peptide sequence.

The peptide sequence for purification which may be used is a peptide sequence conventionally used in the art. The peptide sequence for purification includes, for example, a histidine tag sequence having a consecutive amino acid sequence of at least 4 and preferably at least 6 histidine residues, an amino acid sequence with the binding domain of glutathione S-transferase into glutathione, the amino acid sequence of Protein A, and the like.

The secretory signal peptide is intended to mean a peptide region which has the role of transporting a protein or polypeptide bound to the secretory signal peptide across a cell membrane. The amino acid sequences of such secretory signal peptides and nucleotide sequences encoding the same are well known in the art and reported (see, e.g., von Heijne G (1988) Biochim. Biophys. Acta 947: 307-333, von Heijne G (1990) J. Membr. Biol. 115: 195-201, etc.). More specifically, the secretory signal peptides include, e.g., the secretory signal peptide from the outer membrane protein A of *Escherichia coli* (OmpA) (Ghrayeb, J. et al., (1984) EMBO J. 3: 2437-2442), the secretory signal peptide from cholera toxin obtained from *Vibrio cholerae*, etc.

The mutant apoprotein of the present invention is, for example, a protein comprising the amino acid sequence of SEQ ID NO: 8.

The method for acquiring the mutant apoprotein of the present invention is not particularly limited. The mutant apoprotein of the present invention may be a protein synthesized by chemical synthesis, or a recombinant protein produced by a genetic engineering technique. When the mutant apoprotein of the present invention is to be chemically synthesized, synthesis may be carried out by using, for example, the Fmoc (fluorenylmethyloxycarbonyl) method, the tBoc (t-butyloxycarbonyl) method, or the like. In addition, peptide synthesizers available from AAPPTEC (the former Advanced ChemTech), PerkinElmer, Pharmacia, Protein Technology Instrument, Synthecell-Vega, PerSeptive, Shimadzu Corporation, etc. may also be used for the chemical synthesis. When the mutant apoprotein of the present invention is to be produced by a genetic engineering technique, the mutant apoprotein may be produced by a conventional genetic recombination technique. More specifically, the mutant apoprotein of the present invention may be produced by inserting a polynucleotide (e.g., DNA) encoding the mutant apoprotein of the present invention into a suitable expression system. The polynucleotide encoding the mutant apoprotein of the present invention and expression of the mutant apoprotein of the present invention in an expression system will be later described.

2. Polynucleotide of the Invention

The present invention also provides a polynucleotide encoding the mutant apoprotein of the present invention. The polynucleotide of the present invention may be any polynucleotide as long as it has a nucleotide sequence encoding the mutant apoprotein of the present invention, and preferably, a DNA. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a reverse transcription polymerase chain reaction (hereinafter abbreviated as RT-PCR) using the total RNA or mRNA fraction prepared from the cell or tissue.

The polynucleotide of the present invention includes a polynucleotide encoding the mutant apoprotein comprising an amino acid sequence wherein the 23rd to 34th amino acids in the amino acid sequence of SEQ ID NO: 2 are substituted with an amino acid represented by formula I below: Xaa23-Xaa24-Xaa25-Xaa26-Xaa27-Xaa28-Xaa29-Xaa30-Xaa31-Xaa32-Xaa33-Xaa 34

(wherein,

Xaa23 is Asp, Glu, Gln, Ser, Thr or Asn,

Xaa24 is Lys, Arg, His, Leu or Thr,

Xaa25 is Asp, Glu, Gln, Ser, Thr or Asn,

Xaa26 is an optional amino acid,

Xaa27 is Asp, Glu, Gln, Ser, Thr or Asn,
Xaa28 is Gly,
Xaa29 is an optional amino acid,
Xaa30 is Ile, Leu or Val,
Xaa31 is Asp, Glu, Gln, Ser, Thr or Asn,
Xaa32 is an optional amino acid,
Xaa33 is an optional amino acid, and,
Xaa34 is Asp, Glu, Gln, Ser, Thr or Asn)
having a function to bind to the peroxide of coelenterazine or the peroxide of a coelenterazine analogue to form a photoprotein capable of emitting light under the action of calcium ions; and,
having a half decay time of the luminescence emitted by binding of the photoprotein to calcium ions being longer when compared to native aequorin.

Specific examples of the mutant apoprotein of the present invention are the same as given above.

Preferably, the polynucleotide of the present invention includes the following:

(a) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 15;

(b) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 24;

(c) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 27;

(d) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 33;

(e) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 15;

(f) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 51;

(g) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 63;

(h) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 72;

(i) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 84;

(j) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 75; or, (k) a polynucleotide comprising a polynucleotide wherein the 67th to 102nd nucleotides in the nucleotide sequence of SEQ ID NO: 1 are substituted with the 4th to 39th nucleotides in the nucleotide sequence of SEQ ID NO: 81.

The polynucleotide of the invention can be obtained by introducing mutation into, e.g., the 67th to 102nd nucleotides in the nucleotide sequence of SEQ ID NO: 1 (the nucleotide sequence of aequorin EF hand loop [I]).

The mutation can be introduced into the polynucleotide by introducing the mutation through replacement of, e.g., the nucleotide sequence of aequorin EF hand loop [I] by the nucleotide sequence of aequorin EF hand loop [III] or [IV] or by the nucleotide sequence of EF hand loop in other calcium-binding proteins.

To introduce the mutation, there may also be used a site-directed mutagenesis technique (see, for example, Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), Kunkel, Methods Enzymol. 85, 2763-2766 (1988), etc.), and methods using amber mutation (see, for example, the gapped duplex method described in Nucleic Acids Res. 12, 9441-9456 (1984), etc.).

The mutation may also be introduced into the polynucleotide by PCR using a pair of primers bearing on the respective 5' ends a sequence in which the target mutation (deletion, addition, substitution and/or insertion) is introduced (see, for example, Ho, S. N. et al., Gene 77, 51 (1989), etc.).

The polynucleotide of the present invention is particularly preferably a polynucleotide comprising a polynucleotide encoding a protein consisting of the amino acid sequence of SEQ ID NO: 6. The polynucleotide comprising a polynucleotide encoding a protein consisting of the amino acid sequence of SEQ ID NO: 6 is, for example, a polynucleotide comprising a polynucleotide consisting of the nucleotide sequence SEQ ID NO: 5.

The polynucleotide of the present invention may further contain a polynucleotide encoding an additional peptide sequence at the 5' end and/or 3' end, preferably at the 5' end. The polynucleotide encoding the additional peptide sequence may include, for example, a polynucleotide encoding at least one peptide sequence selected from the group consisting of a peptide sequence for purification, a secretory signal peptide sequence, and the like. The polynucleotide encoding the peptide sequence for purification which may be used includes a polynucleotide comprising a nucleotide sequence encoding a peptide sequence for purification employed in the art. The peptide sequence for purification includes those described above. The polynucleotide encoding a secretory signal peptide which may be used includes a polynucleotide comprising a nucleotide sequence encoding a secretory signal peptide known in the art. The secretory signal peptide includes those described above.

The polynucleotide of the present invention is particularly preferably a polynucleotide comprising a polynucleotide encoding a protein consisting of the amino acid sequence of SEQ ID NO: 8. The polynucleotide comprising a polynucleotide encoding a protein consisting of the amino acid sequence of SEQ ID NO: 8 is, for example, a polynucleotide comprising a polynucleotide consisting of the nucleotide sequence SEQ ID NO: 7.

3. Recombinant Vector and Transformant of the Invention

The present invention further provides the recombinant vector comprising the polynucleotide of the present invention described above and the transformant.

Construction of Recombinant Vector

The recombinant vector of the present invention can be obtained by ligating (inserting) the polynucleotide (DNA) of the invention into a suitable vector. More specifically, the recombinant vector can be obtained by digesting a purified form of the polynucleotide (DNA) with a suitable restriction enzyme and inserting the digestion product into a restriction enzyme site or multicloning site on a suitable vector, thereby ligating the polynucleotide to the vector. The vector for inserting the polynucleotide of the invention is not particularly limited, as far as the vector is capable of replication in a host. Vectors which may be used include plasmids, bacteriophages, animal viruses, etc. Examples of such plasmids include plasmids from *Escherichia coli* (e.g., pBR322, pBR325, pUC118, pUC119, etc.), plasmids from *Bacillus subtilis* (e.g., pUB110, pTP5, etc.), plasmids from yeast (e.g., YEp13, YEp24, YCp50, etc.), and the like. An example of the bacteriophage is a λ phage. Examples of the animal viruses include retroviruses, vaccinia viruses, insect viruses (e.g., baculoviruses, etc.), and the like.

The polynucleotide of the present invention is generally ligated downstream from the promoter of a suitable vector in an expressible manner. Where the host used for transformation is an animal cell, preferred examples of the promoter used include a promoter from SV40, a retrovirus promoter, a metallothionein promoter, a heat shock promoter, a cytomegalovirus promoter, a SRα promoter, etc. Where the host is a bacterium belonging to the genus *Escherichia*, preferred examples of the promoter include a Trp promoter, T7 promoter, lac promoter, recA promoter, λPL promoter, 1pp promoter, etc. Where the host is a bacterium belonging to the *Bacillus*, preferred examples of the promoter include a SPO1 promoter, SPO2 promoter and penP promoter, etc. If the host is yeast, preferred promoters include a PHOS promoter, PGK promoter, GAP promoter, ADH1 promoter and GAL promoter, etc. Where the host is an insect cell, preferred examples of the promoter include a polyhedrin promoter and P10 promoter, etc.

A low-temperature expression-inducible promoter may also be suitably used. Examples of the low-temperature expression-inducible promoter include promoter sequences for cold shock genes, and the like. The cold shock gene includes, for example, *Escherichia coli* cold shock genes (e.g., cspA, cspB, cspG, cspI, csdA, etc.), *Bacillus caldolyticus* cold shock genes (e.g., Bc-Csp, etc.), *Salmonella enterica* cold shock genes (e.g., cspE, etc.), *Erwinia carotovora* cold shock genes (e.g., cspG, etc.), and the like. Among them, a cspA promoter, cspB promoter, cspG promoter, cspI promoter and csdA promoter, etc. can be suitably used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and can be provided for use. The selection marker includes, for example, a dihydrofolate reductase gene, an ampicillin resistance gene, a neomycin resistance gene, etc.

Preparation of Transformant

The thus obtained recombinant vector comprising the polynucleotide of the invention (i.e., the polynucleotide encoding the mutant apoprotein of the invention) is introduced into an appropriate host, and the transformant can be prepared. The host is not particularly limited as long as it is capable of expressing the polynucleotide (DNA) of the invention. For example, the host may be bacteria of the genera *Escherichia, Bacillus, Pseudomonas* and *Rhizobium*, yeast, animal cells or insect cells, etc. Bacteria of the genus *Escherichia* include *Escherichia coli*, etc. Bacteria of the genus *Bacillus* include *Bacillus subtilis*, etc. Bacteria of the genus *Pseudomonas* include, for example, *Pseudomonas putida*, etc. Bacteria of the genus *Rhizobium* include, for example, *Rhizobium meliloti*, etc. Yeast includes, for example, *Saccharomyces cerevisiae, Schizosaccharomyces pombe*, etc. Animal cells include, for example, COS cells, CHO cells, etc. Insect cells include, for example, Sf9, Sf21, etc.

The method of transfecting the recombinant vector into the host and the method of transformation thereby can be performed according to various general methods. The method of transfecting the recombinant vector into the host cell includes, for example, the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes, for example, the method described in Molecular & General Genetics, 168, 111 (1979), etc. The method for transforming yeast includes, for example, the method described in Proc. Natl. Acad. Sci. USA, 75, 1929 (1978), etc. The method for transformation of animal cells includes, for example, the method described in Virology, 52, 456 (1973), etc. The method for transformation of insect cells includes, for example, the method described in Bio/Technology, 6, 47-55 (1988), etc. Thus, the transformant transformed with the recombinant vector comprising the polynucleotide encoding the mutant apoprotein of the invention (i.e., the polynucleotide of the invention) can be acquired.

Expression Vector Comprising Low-Temperature Expression-Inducible Promoter Sequence and Transformant Among them, the expression vector comprising the low-temperature expression-inducible promoter sequence is preferred as the expression vector.

Specifically, the expression vector comprising the low-temperature expression-inducible promoter sequence is intended to mean an expression vector comprising the following promoter sequence and coding sequence:

(1) a low-temperature expression-inducible promoter sequence; and, (2) a coding sequence comprising the polynucleotide of the invention.

The low-temperature expression-inducible promoter sequence is intended to mean a promoter sequence which is capable of inducing expression of the fusion protein by lowering the temperature from the culture conditions under which host cells can grow. Examples of the low-temperature expression-inducible promoter are promoters for genes encoding cold shock proteins (cold shock genes). Examples of the cold shock gene promoters include those as described above.

The temperature at which the low-temperature expression-inducible promoter used in the present invention is expression-inducible is generally 30° C. or less, preferably 25° C. or less, and more preferably 20° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, a pCold I vector, pCold II vector, pCold III vector and pCold IV vector (all manufactured by Takara-Bio), etc. can be suitably used as the vector for insertion of the polynucleotide of the invention. The fusion protein can be produced as a soluble protein in the cytoplasm serving as a host when expression is performed in a prokaryotic host cell using these vectors.

Prokaryotic cells are preferred for the host into which the expression vector comprising the low-temperature expression-inducible promoter sequence is introduced, *Escherichia coli* being more preferred, the BL21 and JM109 strains being particularly preferred. Among them, the BL21 strain is most preferred.

Temperatures for incubation at which cell growth is achieved for the transformant wherein the expression vector comprising the low-temperature expression-inducible promoter sequence is introduced are generally 25 to 40° C. and preferably 30 to 37° C. Temperatures for inducing the expression are generally 4 to 25° C., preferably 10 to 20° C., more preferably 12 to 18° C., and most preferably 15° C.

4. Production of Mutant Apoprotein of the Invention

The present invention further provides a method for producing the mutant apoprotein of the invention, which comprises the steps of culturing the transformant described above to form the mutant apoprotein of the invention. The mutant apoprotein of the invention can be produced by culturing the transformant described above under conditions capable of expressing the polynucleotide (DNA) encoding the mutant apoprotein of the invention, producing and accumulating the mutant apoprotein of the invention, and separating and purifying the resulting product.

Incubation of Transformant

Incubation of the transformant of the invention can be performed in a conventional manner ordinarily used for incubation of a host. Through the incubation, the mutant apoprotein of the invention is produced by the transformant and the mutant apoprotein of the invention is accumulated within the transformant or in the culture medium.

The medium for culturing the transformant using bacteria of the genus *Escherichia* or the genus *Bacillus* as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed by the expression vector using an inducible promoter as the promoter is cultured, an inducer may also be added to the medium, if necessary. For example, when the transformant transformed by an expression vector using a Lac promoter is cultured, isopropyl-β-D-thiogalactopyranoside (IPTG), etc. may be added to the medium and indoleacrylic acid (IAA), etc. may be added to the medium when the transformant transformed by an expression vector using a trp promoter is cultured.

When the host is bacteria of the genus *Escherichia*, the incubation is performed generally at approximately 15 to 43° C. for approximately 3 to 24 hours. If necessary, aeration and agitation may be applied. When the host is bacteria of the genus *Bacillus*, the incubation is performed generally at approximately 30 to 40° C. for approximately 6 to 24 hours. If necessary, aeration and agitation may be applied.

Media for incubation of the transformant when the host is yeast include Burkholder's minimal medium (Proc. Natl. Acad. Sci. USA, 77, 4505 (1980)) and SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20° C. to 35° C. for approximately 24 to 72 hours. If necessary, aeration and agitation may be applied.

Media for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30° C. to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperatures for incubation at which the transformant with the introduced expression vector comprising the low-temperature expression-inducible promoter sequence and temperatures for expression induction are as described above.

Separation and Purification of Mutant Apoprotein of the Invention

The mutant apoprotein of the present invention can be obtained by separating and purifying the mutant apoprotein of the present invention from the culture described above. As used herein, the culture is intended to mean any one of a culture broth, cultured cells or cultured bacteria and cell debris of the cultured cells or cultured bacteria. The mutant apoprotein of the present invention can be separated and purified in a conventional manner.

Specifically, when the mutant apoprotein of the present invention accumulates in the cultured bacteria or cultured cells, after completion of the incubation, the bacteria or cells are disrupted in a conventional manner (e.g., ultrasonication, lysozyme, freezing and thawing, etc,) and then a crude extract of the mutant apoprotein of the present invention can be obtained in a conventional manner (e.g., centrifugation, filtration, etc.). When the mutant apoprotein of the present invention accumulates in the periplasmic space, after completion of the incubation, the extract containing the target protein can be obtained in a conventional manner (e.g., the osmotic shock method, etc.). When the mutant apoprotein of the present invention accumulates in the culture broth, after completion of the incubation, the culture supernatant containing the mutant apoprotein of the present invention can be obtained by separating the bacteria or cells and the culture supernatant in a conventional manner (e.g., centrifugation, filtration, etc.).

The mutant apoprotein of the present invention contained in the extract or culture supernatant thus obtained can be purified by conventional methods of separation and purification. Examples of these separation and purification methods which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. If the mutant apoprotein of the present invention contains the peptide sequence for purification described above, it is preferred to perform the purification using the same. Specifically, when the mutant apoprotein of the present invention contains a histidine tag sequence, nickel chelate affinity chromatography may be used; when the apoprotein contains the binding domain of S-transferase to glutathione, affinity chromatography with a glutathione-binding gel may be used; when the apoprotein contains the amino acid sequence of Protein A, antibody affinity chromatography may be used.

5. Production of Photoprotein of the Invention

The photoprotein of the invention is a photoprotein comprising the mutant apoprotein of the present invention and the peroxide of coelenterazine or the peroxide of a coelenterazine analogue. That is, the photoprotein of the invention is present in such a state that the mutant apoprotein of the present invention forms a complex with the peroxide of coelenterazine or its analogue produced from coelenterazine or its analogue and molecular oxygen. When calcium ions are bound to the photoprotein of the invention, a flash of light emits to form coelenteramide or its analogue as the oxidation product of coelenterazine or its analogue and carbon dioxide.

Examples of coelenterazine or its analogue include coelenterazine, h-coelenterazine, hcp-coelenterazine, cp-coelenterazine, f-coelenterazine, fcp-coelenterazine, n-coelenterazine, Bis-coelenterazine, MeO-coelenterazine, e-coelenterazine, cl-coelenterazine, ch-coelenterazine, 3iso-coelenterazine, 3meo-coelenterazine, cf3-coelenterazine, i-coelenterazine, et-coelenterazine, me-coelenterazine, 3me-coelenterazine, ameh-coelenterazine, etc. In some embodiments of the present invention, coelenterazine is preferred. In some other embodiments of the present invention, n-coelenterazine, cf3-coelenterazine, i-coelenterazine, meo-coelenterazine or me-coelenterazine is preferred. These coelenterazine or coelenterazine analogues may be synthesized according to known methods or are also commercially available.

Coelenterazine or its analogues can be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, Inouye et al. (2010) Anal. Biochem. 407, 247-252, etc., or modifications thereof.

Commercially available coelenterazine or its analogues are coelenterazine and h-coelenterazine manufactured by JNC Corporation; hcp-coelenterazine, cp-coelenterazine, f-coelenterazine, fcp-coelenterazine and n-coelenterazine manufactured by Sigma, Inc., and the like.

The photoprotein of the invention can be produced from the mutant apoprotein of the present invention and coelenterazine or a coelenterazine analogue in the same manner as in known calcium-binding photoproteins (e.g., aequorin, etc.). Specifically, the photoprotein of the present invention can be prepared by the methods described in, e.g., Shimomura O. et al (1988) Biochem. J. 251, 405-410, Shimomura O. et al. Biochem. J. (1989) 261, 913-920, etc.

For example, the purified mutant apoprotein of the present invention can be produced by incubating coelenterazine or its analogue as a light-emitting substrate in the presence of a reducing agent (e.g., mercaptoethanol, dithiothreitol, etc.) and oxygen at low temperatures, thus producing the photoprotein of the invention which emits light dependently on the calcium ion level.

6. Use of Mutant Apoprotein of the Invention and Photoprotein of the Invention

Detection or Quantification of Calcium Ions

The mutant apoprotein of the present invention is a protein that can be produced by forming a non-covalent bond with the peroxide of coelenterazine or the peroxide of a coelenterazine analogue, which is formed from coelenterazine or its analogue and molecular oxygen, and is capable of forming a photoprotein which emits light under the action of calcium ions. Therefore, the mutant apoprotein of the invention and the photoprotein of the invention can be used for detecting or quantifying calcium ions.

When the mutant apoprotein of the invention is used to detect or quantify calcium ions, the photoprotein of the invention is used. The photoprotein of the invention can be produced by the method described above. The detection or quantification of calcium ions can be performed, for example, by adding a sample solution directly to a solution of the photoprotein of the invention and measuring the luminescence generated. Alternatively, calcium ions can also be detected or quantified by adding a solution of the photoprotein of the invention to a sample solution and measuring the luminescence generated.

According to the present invention, the photoprotein of the invention may also be formed by contacting the mutant apoprotein of the invention with coelenterazine or its analogue in the measurement system. As used herein, the term "contact" means that the mutant apoprotein and coelenterazine or its analogue are allowed to be present in the same reaction system, and includes, for example, the states that the mutant apoprotein of the invention is added to a container charged with coelenterazine or its analogue, coelenterazine or its analogue is added to a container charged with the mutant apoprotein of the invention, the mutant apoprotein of the invention is mixed with coelenterazine or its analogue, and the like. The photoprotein of the invention formed is a complex of the mutant apoprotein of the invention and the peroxide of coelenterazine or its analogue. The complex emits light dependently on the calcium ion level and by measuring its luminescence, calcium ions can be detected or quantified.

The detection or quantification of calcium ions can be performed by measuring the luminescence of the photoprotein of the invention through the action of calcium ions using a luminometer. Luminometers which may be used include commercially available instruments, such as a Centro LB 960 (manufactured by Berthold, Inc.), etc. The calcium ion level can be quantitatively determined by preparing a luminescence standard curve for known calcium ion levels using the photoprotein of the present invention.

The mutant apoprotein of the invention may also be used to detect changes in the intracellular calcium ion level under physiological conditions, which involves preparing the photoprotein of the invention and injecting the photoprotein of the invention directly into cells by means of microinjection, etc.

In addition to the introduction by means of microinjection, etc., the mutant apoprotein of the present invention may also be produced in cells, which involves intracellularly expressing a gene for the mutant apoprotein of the present invention (polynucleotide of the present invention). The photoprotein may further be produced by adding coelenterazine or its analogue to the resulting mutant apoprotein of the present invention from the external cells.

Using the photoprotein of the present invention thus introduced into cells or produced in cells, changes in the intracellular calcium ion level caused by external stimulation (e.g., stimulation with receptor-associated drugs, etc.) can also be determined.

Use as Reporter Protein

The mutant apoprotein of the present invention can also be used as a reporter protein to determine the transcription activity of a promoter, etc. The polynucleotide (i.e., the polynucleotide of the present invention) encoding the mutant apoprotein of the present invention is fused to a target promoter or other expression control sequence (e.g., an enhancer, etc.) to construct a vector. The vector described above is transfected to a host cell, and coelenterazine or its analogue is brought in contact with the host cell in the presence of calcium ions or divalent or trivalent ions replaceable for the calcium ions. By detecting the luminescence from the mutant apoprotein of the present invention (i.e., the luminescence from the photoprotein of the present invention), the activity of the target promoter or other expression control sequence can be determined. As used herein, the term "contact" means that a host cell and coelenterazine or its analogue are allowed to be present in the same culture/reaction system, and includes, for example, addition of coelenterazine or its analogue to a culture container charged with a host cell, mixing of a host cell with coelenterazine or its analogue, culture of a host cell in the presence of coelenterazine or its analogue, and the like.

The polynucleotide of the present invention can thus be used as a reporter gene.

Use as Detection Marker Utilizing Luminescence

The mutant apoprotein of the present invention or the photoprotein of the present invention can be used as a marker for detection by luminescence. The detection marker by luminescence can be used to detect a target substance in, e.g., immunoassay, hybridization assay, etc. The mutant apoprotein of the present invention or the photoprotein of the present invention can be used in the form bound to a target substance (protein, nucleic acid, etc.) in a conventional manner including chemical modification. Detection methods using the detection marker can be performed in a conventional manner. The detection marker of the present invention can also be used to determine the distribution of a target substance by expressing the marker, e.g., as a fusion protein of the mutant apoprotein of the present invention and the target substance, then inserting the fusion protein into cells by means of microinjection or the like and contacting them with coelenterazine or its analogue thereby to produce the photoprotein of the present invention. As used herein, the term "contact" means that a host cell and coelenterazine or its analogue are allowed to be present in the same culture/reaction system, and includes, for example, addition of coelenterazine or its analogue to a culture container charged with a host cell, mixing of a host cell with coelenterazine or its analogue, culture of a host cell in the presence of coelenterazine or its analogue, and the like.

The distribution of such a target protein, etc. can be determined by a method for detection such as luminescence imaging. The mutant apoprotein of the present invention can also be used after expression in cells, in addition to the insertion into cells by means of microinjection, etc.

Material for Amusement Supplies

The photoprotein of the present invention emits light only by binding to a trace of calcium ions. The photoprotein of the present invention can thus be preferably used as a luminescence material for amusement supplies. Examples of such amusement supplies are luminescent soap bubbles, luminescent ice, luminescent candies, luminescent color paints, etc. The amusement supplies of the present invention can be prepared in a conventional manner.

Bioluminescence Resonance Energy Transfer (BRET) Method

The photoprotein of the present invention can also be used for analyses including an analysis of biological functions, an assay for enzyme activities, etc., based on the principle of intermolecular interaction by the bioluminescence resonance energy transfer (BRET) method.

For example, using the photoprotein of the present invention as a donor protein and as an acceptor protein an organic compound or a fluorescent protein, the interaction between the proteins can be detected by generating bioluminescence resonance energy transfer (BRET) between them. In some embodiments of the present invention, the organic compound used as the acceptor is Hoechist 3342, Indo-1, DAP1, etc. In some other embodiments of the present invention, the fluorescent protein used as the acceptor is a green fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, G protein-coupled receptor), apoptosis, transcription regulation by gene expression, etc. In another preferred embodiment of the present invention, the enzyme to be analyzed is protease, esterase, kinase, etc.

Analysis of the physiological functions by the BRET method may be performed by known methods, for example, by modifications of the methods described in Biochem. J. 2005, 385, 625-637, Expert Opin. Ther. Targets, 2007 11: 541-556, etc. Assay for the enzyme activities may also be performed by known methods, for example, by modifications of the methods described in Nat. Methods 2006, 3:165-174, Biotechnol. J. 2008, 3: 311-324, etc.

7. Fluorescent Protein of the Invention

The fluorescent protein of the present invention is a complex in which coelenteramide or its analogue is coordinated to the mutant apoprotein of the present invention. The fluorescent protein of the present invention is capable of generating fluorescence upon excitation of light. In an embodiment of the present invention, the fluorescent protein (hereinafter sometimes referred to as "the BFP-like protein of the present invention") comprises the mutant apoprotein of the present invention, coelenteramide or its analogue and calcium ions or divalent or trivalent ions replaceable for the calcium ions. In another embodiment of the present invention, the fluorescent protein (hereinafter sometimes referred to as "the gFP-like protein of the present invention") comprises the mutant apoprotein of the present invention and coelenteramide or its analogue but does not contain calcium ions or divalent or trivalent ions replaceable for the calcium ions.

In some embodiments of the present invention, the fluorescent protein has both bioluminescence spectra and fluorescence spectra and, for example, the maximum fluorescence wavelength are shifted toward the longer wavelength side, as compared with the maximum emission wavelength.

According to the present invention, the fluorescent protein is prepared from coelenteramide or its analogue as follows. That is, the mutant apoprotein of the present invention is reacted with coelenteramide or its analogue in the presence or absence of calcium ions or divalent or trivalent ions replaceable for the calcium ions to prepare the fluorescent protein.

According to the present invention, coelenteramide or its analogues used to prepare the fluorescent protein are, e.g., compounds described in the pamphlet of WO 2005/01463, page 6, line 15-page 7, line 23; compounds described in the pamphlet of WO 010/090318, page 9, line 10 to page 10, line 23; etc.

According to the present invention, coelenteramide or its analogues used to prepare the fluorescent protein are more preferably coelenteramide, e-coelenteramide, ch-coelenteramide, etc.

Coelenteramide or its analogues may be prepared by, for example, the method described in Shimomura & Johnson, *Tetrahedron Lett.* (1973) 2963-2966, the method described in Teranishi & Goto Bull. Chem. Soc. Jpn. (1990) 63: 3132-3140, the method described in Shimomura & Teranishi Luminescence (2000) 15:51-58, the method described in the pamphlet of WO 2010/090138, page 22, line 5 from the bottom to page 26, line 6 from the bottom, etc., or modifications of these methods.

The amount of coelenteramide or its analogue used to prepare the fluorescent protein is not particularly limited and is, e.g., 1 mol to 5 mol, preferably 1 mol to 2 mol, and more preferably 1 mol to 1.2 mol, based on 1 mol of the mutant apoprotein of the invention.

In some embodiments of the present invention, calcium ions or divalent or trivalent ions replaceable for the calcium ions are used to produce the BFP-like protein of the present invention. As used herein, the calcium ions or divalent or trivalent ions replaceable for the calcium ions refer to ions which trigger the luminescence reaction when they react with the calcium-binding photoprotein, in place of calcium ions. In other words, they are ions that exert the function similar to calcium ions on the calcium-binding photoprotein. Examples of the calcium ions or divalent or trivalent ions replaceable for the calcium ions include calcium ions ($Ca^{2+}$), magnesium ions ($Mg^{2+}$), strontium ions ($Sr^{2+}$), barium ions ($Ba^{2+}$), lead ions ($Pb^{2+}$), cobalt ions ($Co^{2+}$), nickel ions ($Ni^{2+}$), cadmium ions ($Cd^{2+}$), yttrium ions ($Y^{3+}$), lanthanum ions ($La^{3+}$), samarium ions ($Sm^{3+}$), europium ions ($Eu^{3+}$), dysprosium ions ($Dy^{3+}$), thulium ions ($Tm^{3+}$), ytterbium ions ($Yb^{3+}$), and the like. Among these ions, the divalent metal ions are preferred, more preferably the divalent metal ions other than transition metals, e.g., $Ca^{2+}$, $Sr^{2+}$, $Pb^{2+}$, etc.

The amount of calcium ions or divalent or trivalent ions replaceable for the calcium ions is not particularly limited, and is, e.g., 4 mol to 10 mol, 10 mol to 100 mol, 100 mol to 1000 mol, etc., based on 1 mol of the mutant apoprotein of the invention.

In producing the fluorescent protein of the present invention, the reaction of the mutant apoprotein of the present invention with coelenteramide or its analogue is carried out preferably in the presence of a reducing agent. Examples of the reducing agent used herein include dithiothreitol (DTT), mercaptoethanol, etc. The amount of the reducing agent used to produce the fluorescent protein of the invention is not particularly limited, so long as the amount does not affect the regeneration of the fluorescent protein of the invention. Where two or more cysteine residues are present on the mutant apoprotein of the invention, the concentration is preferably sufficient to prevent the S—S bonds. The concentration is, for example, 1 mM dithiothreitol or 0.1% (v/v) mercaptoethanol in a final concentration.

In some embodiments of the present invention, to produce the gFP-like protein of the invention, the reaction of the mutant apoprotein of the present invention with coelenteramide or its analogue is carried out in the absence of calcium ions or divalent or trivalent ions replaceable for the calcium ions and in the presence of a chelating agent for sequestering calcium ions or divalent or trivalent ions replaceable for the calcium ions. In this case, the amount of the chelating agent is not particularly limited unless its concentration affects the production of the fluorescent protein. Since it is demonstrated that 3 mols of calcium ions bind to 1 mol of the mutant apoprotein of the invention in its ionic state, e.g., 3 mols or more are preferred.

The chelating agent used to produce the gFP-like protein of the present invention is not particularly limited, so long as it strongly binds to calcium ions or divalent or trivalent ions replaceable for the calcium ions. Examples of the chelating agent include ethylenediaminetetraacetic acid (EDTA), ethylene glycol-bis(β-aminoethyl ether)-N,N,N',N'-tetraacetic acid (EGTA), trans-1,2-diaminocyclohexane-N,N,N',N'-tetraacetic acid (CyDTA), N-(2-hydroxyethyl)iminodiacetic acid (HIDA) and the like.

In producing the fluorescent protein of the present invention, the reaction temperature and reaction time are not particularly limited but are generally at 0° C. to 42° C. for 0.1 to 2 hours, at 4° C. to 37° C. for 0.1 to 2 hours, or at 4° C. to 15° C. for 0.1 to 24 hours.

The fluorescent protein of the invention thus produced may be further purified. Purification of the fluorescent protein of the invention can be performed in a conventional manner of separation and purification. The separation and purification include, for example, precipitation with ammonium sulfate, gel filtration chromatography, ion exchange chromatography, affinity chromatography, reversed phase high performance liquid chromatography, dialysis, ultrafiltration, etc., alone or in an appropriate combination of these techniques.

8. Use of Fluorescent Protein of the Invention

Use as Luminescent Catalyst

The BFP-like protein of the present invention acts on a light-emitting substrate to emit light from the substrate and can be used as a luminescent catalyst. Therefore, the present invention provides a method for emitting light, which comprises contacting the BFP-like protein of the present invention with coelenterazine or its analogue. As used herein, the term "contact" means that the BFP-like protein of the present invention and coelenterazine or its analogue are allowed to be present in the same reaction system, and includes, for example, addition of the BFP-like protein of the present invention to a container charged with coelenterazine or its analogue, addition of coelenterazine or its analogue to a container charged with the BFP-like protein of the present invention, mixing of the BFP-like protein of the present invention with coelenterazine or its analogue, and the like.

The light-emitting substrate used in the method for light emission according to the present invention is, for example, coelenterazine or its analogue. The analogue of coelenterazine includes the same as described above.

These coelenterazine and analogues thereof are brought in contact with the BFP-like fluorescent protein of the invention. By the catalytic action of the BFP-like protein contacted, coelenterazine or its analogue is oxidized to the corresponding coelenteramide or its analogue, whereby luminescence generates (at this time carbon dioxide is released). The luminescence time is generally 0.5 to 3 hours. However, the luminescence time can be further prolonged or more shortened, depending upon conditions chosen.

Use as Reporter Protein

The BFP-like fluorescent protein of the present invention can also be used as a reporter protein to determine the transcription activity of a promoter, etc. A polynucleotide encoding the mutant apoprotein of the present invention is fused to a target promoter or other expression control sequence (e.g., an enhancer, etc.) to construct a vector. The vector described above is transfected to a host cell, and coelenteramide or its analogue is brought in contact with the host cell in the presence or absence of calcium ions or divalent or trivalent ions replaceable for the calcium ions. By detecting the fluorescence from the fluorescent protein of the present invention, the activity of the target promoter or other expression control sequence can be determined. As used herein, the term "contact" means that a host cell and coelenteramide or its analogue are allowed to be present in the same culture system/reaction system, and includes, for example, addition of coelenteramide or its analogue to a culture container charged with a host cell, mixing of a host cell with coelenteramide or its analogue, culture of a host cell in the presence of coelenteramide or its analogue, and the like.

Use as Detection Marker

The fluorescent protein of the present invention can be used as a marker for detection by fluorescence. The detection marker of the present invention can be used to detect a target substance in, e.g., immunoassay, hybridization assay, etc. The fluorescent protein of the present invention can be used in the form bound to a target substance (protein, nucleic acid, etc.) in a conventional manner including chemical modification, etc. Detection methods using such a detection marker can be performed in a conventional manner.

The detection marker of the present invention can also be used to determine the distribution of a target substance by expressing the marker as, e.g., a fusion protein of the mutant apoprotein of the present invention and the target substance, then inserting the fusion protein into cells by means of microinjection or the like and contacting them with coelenteramide or its analogue in the presence or absence of calcium ions or divalent or trivalent ions replaceable for the calcium ions. As used herein, the term "contact" means that cells and coelenteramide or its analogue are allowed to be present in the same culture system/reaction system, and includes, for example, addition of coelenteramide or its analogue to a culture container charged with cells, mixing of cells with coelenteramide or its analogue, culture of host cells in the presence of coelenteramide or its analogue, and the like.

The distribution of such a target substance, etc. can be determined by a method for detection such as fluorescence imaging, etc. The mutant apoprotein of the present invention may also be used after its expression in cells, in addition to the insertion into cells by means of microinjection, etc.

Material for Amusement Supplies

When excited by light, the fluorescent protein of the invention emits fluorescence upon excitation of light. Therefore, the fluorescent protein of the present invention can be preferably used as a fluorescence material for amusement supplies. Examples of such amusement supplies are fluorescent soap bubbles, fluorescent ice, fluorescent candies, fluorescent color paints, etc. The amusement supplies of the invention can be prepared in a conventional manner.

Fluorescence Resonance Energy Transfer (FRET) Method

The fluorescent protein of the present invention can be used for analyses including an analysis of biological functions, an analysis of (assay for) enzyme activities, etc., based on the principle of intermolecular interactions by the fluorescence resonance energy transfer (FRET) method.

For example, using the fluorescent protein of the invention as a donor or an acceptor and an organic compound or another fluorescent protein as an acceptor or a donor, the interaction between the proteins can be detected by causing fluorescence resonance energy transfer (FRET) between them. In some embodiments of the present invention, the organic compound used as an acceptor or a donor is Hoechst 3342, Indo-1, DAPI, etc. In some other embodiments of the present invention, another fluorescent protein used as an acceptor or a donor is another green fluorescent protein (GFP), another blue fluorescent protein (BFP), another mutant GFP fluorescent protein, phycobilin, etc. In a preferred embodiment of the present invention, the physiological functions to be analyzed include an orphan receptor (in particular, G protein-coupled receptor), apoptosis, transcription regulation by gene expression, etc. In a preferred embodiment of the present invention, the enzyme to be analyzed is protease, esterase, kinase, etc.

Analysis of the physiological functions by the FRET method may be performed by known methods, for example, by modifications of the methods described in Hoffmann, C. et al. *Nat Methods* (2005) 2: 171-176, Paulsson, J. F. et al. *Exp. Diabetes Res.* 2008: 2008, 865850, etc. Assay for the enzyme activity may also be performed by known methods, for example, by modifications of the methods described in Ting, A. Y. et al (2001) *Proc. Natl. Acad. Sci. USA* 98: 15003-15008, Evellin, S. et al (2004) *Methods. Mol. Biol.* 284: 259-270, Palmer A. E. & Tsien, R. Y. (2006) 1:1057-1065, etc.

9. Kit of the Invention

The present invention also provides a kit comprising at least one selected from the mutant apoprotein of the present invention, the polynucleotide of the invention, the recombinant vector of the invention and the transformant of the invention, the photoprotein of the invention, the fluorescent protein of the invention, and the like.

In an embodiment of the present invention, the kit comprises the mutant apoprotein of the present invention or the photoprotein of the present invention. In another embodiment of the present invention, the kit comprises the polynucleotide of the present invention, the recombinant vector of the invention or the transformant of the invention.

The kit may further contain at least one selected from coelenterazine or its analogue and coelenteramide or its analogue. The kit of the present invention can be prepared with conventional materials by conventional methods. The kit of the present invention may further contain sample tubes, plates, instructions for the kit user, solutions, buffers, reagents, and samples suitable for standardization or control samples.

The kit of the present invention can be used for the aforesaid detection or quantification of calcium ions, or the measurement using the reporter protein or reporter gene, or as a luminescence marker, a fluorescence marker, etc.

10. Method for Screening Mutant Apoprotein

The present invention provides a method for screening a mutant apoprotein capable of forming a calcium-binding photoprotein with low calcium sensitivity (hereinafter sometimes referred to as "the screening method of the present invention). The screening method of the present invention comprises the following steps:

(1) the step of constructing a mutant apoprotein wherein the loop of EF hand in calcium-binding domain I of apoaequorin is replaced by:

(a) the loop of EF hand in calcium-binding domain III or IV of apoaequorin, or, (b) the loop of any one of EF hands in calcium-binding domains of a calcium-binding protein, which is different from apoaequorin;

(2) the step of determining a half decay time of the luminescence from the calcium-binding photoprotein formed by the mutant apoprotein; and, (3) the step of selecting a mutant apoprotein of a calcium-binding photoprotein as the mutant apoprotein capable of forming the calcium-binding photoprotein with low calcium sensitivity when the half decay time of the luminescence from the calcium-binding photoprotein is not less than 2 seconds.

In the step (1), there is produced a mutant apoprotein wherein the loop of EF hand in calcium-binding domain I of apoaequorin is replaced by a different EF hand loop. The replacement of the loop of EF hand in calcium-binding domain I of apoaequorin by other EF hand loop can be achieved by known methods. An example includes a method using the expression vector pAM2+X later described in EXAMPLE.

The calcium-binding domain I of apoaequorin is replaced by (a) the loop of EF hand in calcium-binding domain III or IV of apoaequorin, or, (b) the loop of any one of EF hands in calcium-binding domains of a calcium-binding protein, which is different from apoaequorin. Examples of the calcium-binding protein different from apoaequorin include clytin I, clytin II, mitrocomin, Renilla luciferin binding protein (RLBP), calmodulin, sacroplasmic calcium-binding protein (SCBP), troponin C, parvalbumin, calpain, S100, etc.

In the step (2), there is determined a half decay time of the luminescence from the calcium-binding photoprotein formed by the mutant apoprotein. The half decay time of the luminescence is a time period until the luminescence intensity of the photoprotein reaches half of the maximum luminescence intensity. The half decay time can be determined by the procedure described above.

In the step (3), when the half decay time of the luminescence from the calcium-binding photoprotein determined above is not less than 2 seconds, the mutant apoprotein of the calcium-binding photoprotein is selected as a mutant apoprotein capable of forming the calcium-binding photoprotein with low calcium sensitivity. The term "not less than 2 seconds" is, for example, 2 seconds or more, 2.1 seconds or more, 2.2 seconds or more, 2.3 seconds or more, 2.4 seconds or more, 2.5 seconds or more, 2.6 seconds or more, 2.7 seconds or more, 2.8 seconds or more, 2.9 seconds or more, 3.0 seconds or more, 3.1 seconds or more, 3.2 seconds or more, 3.3 seconds or more, 3.4 seconds or more, 3.5 seconds or more, 3.6 seconds or more, 3.7 seconds or more, 3.8 seconds or more, 3.9 seconds or more, 4.0 seconds or more, or 4.1 seconds or more. More preferably, the term "not less than 2 seconds" is not less than each of these values and 100 seconds or less, 70 seconds or less, 50 seconds or less, 40 seconds or less, 30 seconds or less, 29 seconds or less, 28 seconds or less, 27 seconds or less, 26 seconds or less, 25 seconds or less, 24 seconds or less, 23 seconds or less, 22 seconds or less, or 21.9 seconds or less.

The mutant apoprotein capable of forming the calcium-binding photoprotein with low calcium sensitivity can be screened as described above.

In the embodiments and examples to implement the invention, the methods described in standard protocols such as J. Sambrook, E. F. Fritsch & T. Maniatis (Ed.), Molecular cloning, a laboratory manual (3$^{rd}$ edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., or modifications or alternations thereof may be used unless otherwise indicated therein. When commercially available reagent kits or measurement devices are employed, the protocols attached thereto are used.

All literatures and publications mentioned in this specification are herein incorporated in their entirety by reference into the specification, irrespective of their purposes. The disclosure of the specification, the claims, abstract and drawings of Japanese Application JP2011-083968 filed on Apr. 5, 2011, based upon which the present application claims the benefit of priority, are entirely incorporated herein by reference.

The objects, characteristics, advantages of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is apparent to those skilled in the art that various modifications may be made based on the descriptions given herein within the intent and scope of the present invention disclosed herein.

EXAMPLES

Hereinafter, the present invention will be illustrated more specifically with reference to EXAMPLES, but the invention is not deemed to be limited to these EXAMPLES.

Example 1

Construction of Expression Vector (1) Construction of Novel Expression Vector pAM2+X Novel expression vector pAM2+X was constructed for the purpose of replacing the first EF hand loop sequence (EF hand loop sequence of domain I) of apoaequorin by a different EF hand loop sequence. That is, novel expression vector pAM2+X capable of replacing the nucleotide sequence at the XbaI-AccI region in apoaequorin gene introduced the XbaI stie by other nucleotide was constructed by the following procedure. The XbaI restriction enzyme site was introduced by PCR using site-directed mutagenesis according to the method described in Ho et al., Gene (1989) 77: 51-59. Specifically, PCR (cycle conditions: 25 cycles; 1 min./94° C., 1 min./50° C., 1 min./72° C.) was performed with a PCR kit (manufactured by Takara Bio Inc.) using piQ92-HE having the apoaequorin gene as a template with the following two PCR primers RV-M and Aq-2, according to the method described in Inouye et al. Biochemistry (1986) 25: 8425-8429.

```
RV-M
                                           (SEQ ID NO: 9)
(5' GAG CGG ATA ACA ATT TCA CAC AGG 3')

Aq-2
                                           (SEQ ID NO: 10)
(5' CC ATT GTG GTT GAC ATC TAG AAA ATT G 3')
```

Likewise, PCR was performed with the PCR kit using piQ92-HE as a template with the following two PCR primers Aq-1 and M13-47.

```
Aq-1
                                           (SEQ ID NO: 11)
(5' AAG CAT ATG TTC AAT TTT CTA GAT GTC 3')

M13-47
                                           (SEQ ID NO: 12)
(5' CGC CAG GGT TTT CCC AGT CAC GAC 3')
```

Using the DNA fragments obtained above from two regions as a template, PCR was performed with the PCR kit using the PCR primers RV-M and M13-47 to amplify the aequorin gene region having the desired XbaI site. The DNA fragment obtained was purified with a PCR purification kit (manufactured by Qiagen Inc.). After digestion with the restriction enzymes HindIII/EcoRI in a conventional manner, the digestion product was ligated at the restriction enzyme HindIII/EcoRI site of pUC9-2 described in Hanna, Z. Fregeau, C. Préfontaine, G. and Brousseau, R. Gene (1984) 30: 247-250 to construct pAM2+X. The DNA sequence inserted was confirmed by determining the nucleotide sequence using a DNA sequencer (manufactured by ABI Inc.). The DNA sequence of the expression vector pAM2+X is shown by SEQ ID NO: 3. The amino acid sequence of the protein encoded by the DNA sequence of the expression vector pAM2+X is also shown by SEQ ID NO: 4. The DNA sequence (the 25th to 591st DNA sequence in SEQ ID NO: 3) of apoaequorin in the expression vector pAM2+X is shown by SEQ ID NO: 1. The DNA sequence (the 9th to 196th amino acid sequence in SEQ ID NO: 4) of apoaequorin encoded by SEQ ID NO: 1 is shown by SEQ ID NO: 2.

(2) Construction of Expression Vector in which First EF Hand Loop Sequence (Loop Sequence of EF Hand in Domain I) in Apoaequorin is Replaced by Different EF Hand Loop Sequence Expression vectors, in which the first EF hand loop sequence of apoaequorin for the calcium-binding was replaced with the third and fourth calcium binding EF hand loop sequences of apoaequorin (the loop sequence of EF hand in domain III or IV) or with the EF hand loop sequence of different calcium-binding protein, were constructed by the procedure shown in FIG. 1. That is, these expression vectors were produced by inserting synthetic oligonucleotide corresponding to the amino acids in the EF hand loop sequence of domain III or IV in apoaequorin or in the EF hand loop sequence in an additional calcium-binding protein into the XbaI/AccI site in the expression vector pAM2+X produced in (1) above. Specifically, the following oligonucleotide linkers Aq-9 and Aq-10, which are the XbaI/AccI site in the third EF hand loop sequence (SEQ ID NO: 14 (DIDESGQLDVDE)) of apoaequorin were synthesized. After digestion of pAM2+X with the restriction enzymes XbaI and AccI in a conventional manner, the oligonucleotide linkers Aq-9 and Aq-10 were inserted into the XbaI/AccI site to construct the expression vector pAM20.

Aq-9
(SEQ ID NO: 15)
(5' CTA GAC AAA GAT CAA AAT GGC GCC ATT ACA CTG GAT GAA ATG GT 3')

Aq-10
(SEQ ID NO: 16)
(5' AGA CCA TTT CAT CCA GTG TAA TGG CGC CAT TTT GAT CTT TGT 3')

The expression vectors pAM21, pAM15, pAM22, pAM23, pAM27, pAM28, pAM29, pAM30, pAM31, pAM32, pAM17, pAM33, pAM34, pAM7, pAM24, pAM19, pAM25, pAM16, pAM35, pAM36, pAM37, pAM38 and pAM39, in which the hand loop [I] was replaced by the loop sequence of the EF hands in additional calcium-binding proteins shown in TABLE 1, were constructed by the same procedure. The synthetic oligonucleotides used are shown in TABLE 2.

TABLE 1

List of Mutant Apoproteins with Replaced EF Hand Loops for EF Hand Loop [I] Constructed in EXAMPLE 1

| Vector | EF Hand Loop Sequence | Origin of EF Hand |
|---|---|---|
| pAM2 + X | DVNHNGKISLDE (SEQ ID NO: 13) | aequorin EF hand loop sequence [I] |
| pAM20 | DKDQNGAITLDE (SEQ ID NO: 14) | aequorin EF hand loop sequence [III]-derived |
| pAM21 | DIDESGQLDVDE (SEQ ID NO: 17) | aequorin EF hand loop sequence [IV]-derived |
| pAM15 | DINGDGKITLDE (SEQ ID NO: 20) | clytin-I EF hand loop sequence [I]-derived |
| pAM22 | DKDASGSISLDE (SEQ ID NO: 23) | clytin-I EF hand loop sequence [III]-derived |
| pAM23 | DLDNSGKLDVDE (SEQ ID NO: 26) | clytin-I EF hand loop sequence [IV]-derived |
| pAM27 | DINGNGKITLDE (SEQ ID NO: 29) | clytin-II EF hand loop sequence [I]-derived |
| pAM28 | DKDASGSISLDE (SEQ ID NO: 32) | clytin-II EF hand loop sequence [III]-derived |
| pAM29 | DLDNSGKLDVDE (SEQ ID NO: 35) | clytin-II EF hand loop sequence [IV]-derived |
| pAM30 | DINSNGQINLNE (SEQ ID NO: 38) | mitrocomin EF hand loop sequence [I]-derived |
| pAM31 | DKDRNGSVSLDE (SEQ ID NO: 41) | mitrocomin EF hand loop sequence [III]-derived |
| pAM32 | DLDGDGKLDVDE (SEQ ID NO: 44) | mitrocomin EF hand loop sequence [IV]-derived |

TABLE 1-continued

List of Mutant Apoproteins with Replaced EF Hand Loops for EF Hand Loop [I] Constructed in EXAMPLE 1

| Vector | EF Hand Loop Sequence | Origin of EF Hand |
|---|---|---|
| pAM17 | DVTGDGFISRED (SEQ ID NO: 47) | RLBP EF hand loop sequence [I]-derived |
| pAM33 | DTDKDGYVSLPE (SEQ ID NO: 50) | RLBP hand loop sequence [III]-derived |
| pAM34 | DFNKNGQISRDE (SEQ ID NO: 53) | RLBP hand loop sequence [IV]-derived |
| pAM7 | DKDGDGTITTKE (SEQ ID NO: 56) | calmodulin EF hand loop sequence [I]-derived |
| pAM24 | DADGNGTIDFPE (SEQ ID NO: 59) | calmodulin EF hand loop sequence [II]-derived |
| pAM19 | DKDGNGYISAAE (SEQ ID NO: 62) | calmodulin EF hand loop sequence [III]-derived |
| pAM25 | DIDGDGQVNYEE (SEQ ID NO: 65) | calmodulin EF hand loop sequence [IV]-derived |
| pAM16 | DFDKDGAITRMD (SEQ ID NO: 68) | SCBP EF hand loop sequence [I]-derived |
| pAM35 | DKNHNGAISLDE (SEQ ID NO: 71) | aequorin EF hand loop sequence [I] mutagenesis |
| pAM36 | DRNHNGKISLDE (SEQ ID NO: 74) | aequorin EF hand loop sequence [I] mutagenesis |
| pAM37 | DVNHNGAISLDE (SEQ ID NO: 77) | aequorin EF hand loop sequence [I] mutagenesis |
| pAM38 | DRNHNGAISLDE (SEQ ID NO: 80) | aequorin EF hand loop sequence [I] mutagenesis |
| pAM39 | DKNHNGKISLDE (SEQ ID NO: 83) | aequorin EF hand loop sequence [I] mutagenesis |

TABLE 2

List of Primers Used to Replace for EF Hand Loop [I]

| Vector | EF Hand Loop Sequence | Primer | | Sequence |
|---|---|---|---|---|
| pAM2 + X | DVNHNGKISLDE (SEQ ID NO: 13) (aequorin EF hand loop sequence [I]) | a | Aq-1 | 5' AAG CAT ATG TTC AAT TTT CTA GAT GTC 3' (SEQ ID NO: 11) |
| | | b | Aq-2 | 5' CC ATT GTG GTT GAC ATC TAG AAA ATT G 3' (SEQ ID NO: 10) |
| pAM20 | DKDQNGAITLDE (SEQ ID NO: 14) (aequorin EF hand loop sequence [III]-derived) | a | AQ-9 | 5' CTA GAC AAA GAT CAA AAT GGC GCC ATT ACA CTG GAT GAA ATG GT 3' (SEQ ID NO: 15) |
| | | b | AQ-10 | 5' AGA CCA TTT CAT CCA GTG TAA TGG CGC CAT TTT GAT CTT TGT T 3' (SEQ ID NO: 16) |
| pAM21 | DIDESGQLDVDE (SEQ ID NO: 17) (aequorin EF hand loop sequence [IV]-derived) | a | Aq-11 | 5' CTA GAT ATC GAT GAA AGT GGA CAA CTC GAC GTC GAT GAG ATG GT 3' (SEQ ID NO: 18) |
| | | b | Aq-12 | 5' AGA CCA TCT CAT CGA CGT CGA GTT GTC CAC TTT CAT CGA TAT 3' (SEQ ID NO: 19) |
| pAM15 | DINGDGKITLDE (SEQ ID NO: 20) (clytin-I EF hand loop sequence [I]-derived) | a | PH-52 | 5' CTA GAC ATT AAT GGC GAC GGA AAA ATC ACT TTG GAT GAA ATG GT 3' (SEQ ID NO: 21) |
| | | b | PH-53 | 5' AGA CCA TTT CAT CCA AAG TGA TTT TCC GTC GCC ATT AAT GT 3' (SEQ ID NO: 22) |

TABLE 2-continued

List of Primers Used to Replace for EF Hand Loop [I]

| Vector | EF Hand Loop Sequence | Primer | | Sequence |
|---|---|---|---|---|
| pAM22 | DKDGSGSISLDE (SEQ ID NO: 23) (clytin-I EF hand loop sequence [III]-derived) | a | PH-55 | 5' CTA GAC AAA GAC GGA AGT GGC TCG ATA TCA TTG GAC GAA ATG GT 3' (SEQ ID NO: 24) |
| | | b | PH-56 | 5' AGA CCA TTT CGT CCA ATG ATA TCG AGC CAC TTC CGT CTT TGT 3' (SEQ ID NO: 25) |
| pAM23 | DLDNSGKLDVDE (SEQ ID NO: 26) (clytin-I EF hand loop sequence [IV]-derived) | a | PH-57 | 5' CTA GAT TTG GAC AAC AGT GGC AAA CTT GAT GTC GAC GAG ATG GT 3' (SEQ ID NO: 27) |
| | | b | PH-58 | 5' AGA CCA TCT CGT CGA CAT CAA GTT TGC CAC TGT TGT CCA AAT 3' (SEQ ID NO: 28) |
| pAM27 | DINGNGKITLDE (SEQ ID NO: 29) (clytin-II EF hand loop sequence [I]-derived) | a | PH-59 | 5' CTA GAT ATC AAC GGT AAT GGG AAA ATC ACA TTA GAT GAA ATG GTC TAC 3' (SEQ ID NO: 30) |
| | | b | PH-60 | 5' A GAC CAT TTC ATC TAA TGT GAT TTT CCC ATT ACC GTT GAT AT 3' (SEQ ID NO: 31) |
| pAM28 | DKDASGSISLDE (SEQ ID NO: 32) (clytin-II EF hand loop sequence [III]-derived) | a | PH-61 | 5' CTA GAC AAA GAC GCA AGT GGC TCG ATA TCT TTA GAC GAA ATG GTC TAC 3' (SEQ ID NO: 33) |
| | | b | PH-62 | 5' A GAC CAT TTC GTC TAA AGA TAT CGA GCC ACT TGC GTC TTT GT 3' (SEQ ID NO: 34) |
| pAM29 | DLDNSGKLDVDE (SEQ ID NO: 35) (clytin-II EF hand loop sequence [IV]-derived) | a | PH-63 | 5' CTA GAT TTG GAC AAC AGT GGC AAA CTT GAT GTC GAC GAG ATG GTC TAC 3' (SEQ ID NO: 36) |
| | | b | PH-64 | 5' A GAC CAT CTC GTC GAC ATC AAG TTT GCC ACT GTT GTC CAA AT 3' (SEQ ID NO: 37) |
| pAM30 | DINSNGQINLNE (SEQ ID NO: 38) (mitrocomin EF hand loop sequence [I]-derived) | a | MI-1 | 5' CTA GAT ATC AAT TCA AAT GGC CAA ATC AAT CTG AAT GAA ATG GTC TAC 3' (SEQ ID NO: 39) |
| | | b | MI-2 | 5' A GAC CAT TTC ATT CAG ATT GAT TTG GCC ATT TGA ATT GAT AT 3' (SEQ ID NO: 40) |
| pAM31 | DKDRNGSVSLDE (SEQ ID NO: 41) (mitrocomin EF hand loop sequence [III]-derived) | a | MI-3 | 5' CTA GAC AAA GAT AGA AAT GGA TCC GTT TCG TTA GAC GAA ATG GTC TAC 3' (SEQ ID NO: 42) |
| | | b | MI-4 | 5' A GAC CAT TTC GTC TAA CGA AAC GGA TCC ATT TCT ATC TTT GT 3' (SEQ ID NO: 43) |
| pAM32 | DLDGDGKLDVDE (SEQ ID NO: 44) (mitrocomin EF hand loop sequence [IV]-derived) | a | MI-5 | 5' CTA GAT TTA GAT GGT GAC GGT AAA CTT GAT GTC GAC GAA ATG GTC TAC 3' (SEQ ID NO: 45) |
| | | b | MI-6 | 5' A GAC CAT TTC GTC GAC ATC AAG TTT ACC GTC ACC ATC TAA AT 3' (SEQ ID NO: 46) |
| pAM17 | DVTGDGFISRED (SEQ ID NO: 47) (RLBP EF hand loop sequence [I]-derived) | a | RLBP-4 | 5' CTA GAT GTC ACC GGC GAT GGA TTC ATC TCT CGA GAG GAC ATG GT 3' (SEQ ID NO: 48) |
| | | b | RLBP-5 | 5' AGA CCA TGT CCT CTC GAG AGA TGA ATC CAT CGC CGG TGA CAT 3' (SEQ ID NO: 49) |
| pAM33 | DTDKDGYVSLPE (SEQ ID NO: 50) (RLBP EF hand loop sequence [III]-derived) | a | RLBP-6 | 5' CTA GAT ACT GAT AAA GAT GGT TAT GTT TCT TTA CCC GAG ATG GTC TAC 3' (SEQ ID NO: 51) |
| | | b | RLBP-7 | 5' A GAC CAT CTC GGG TAA AGA AAC ATA ACC ATC TTT ATC AGT AT 3' (SEQ ID NO: 52) |
| pAM34 | DFNKNGQISRDE (SEQ ID NO: 53) (RLBP EF hand loop sequence [IV]-derived) | a | RLBP-8 | 5' CTA GAT TTT AAT AAA AAT GGC CAG ATA TCT CGT GAT GAG ATG GTC TAC 3' (SEQ ID NO: 54) |
| | | b | RLBP-9 | 5' A GAC CAT CTC ATC ACG AGA TAT CTG GCC ATT TTT ATT AAA AT 3' (SEQ ID NO: 55) |
| pAM7 | DKDGDGTTTTKE (SEQ ID NO: 56) (calmodulin EF hand loop sequence [I]-derived) | a | CAL-1 | 5' CTA GAT AAA GAC GGC GAT GGC ACC ATC ACA ACA AAG GAA ATG GT 3' (SEQ ID NO: 57) |
| | | b | CAL-2 | 5' AGA CCA TTT CCT TTG TTG TGA TGG TGC CAT CGC CGT CTT TAT 3' (SEQ ID NO: 58) |

TABLE 2-continued

List of Primers Used to Replace for EF Hand Loop [I]

| Vector | EF Hand Loop Sequence | Primer | | Sequence |
|---|---|---|---|---|
| pAM24 | DADGNGTIDFPE (SEQ ID NO: 59) (calmodulin EF hand loop sequence [II]-derived) | a | CAL-9 | 5' CTA GAC GCT GAT GGT AAT GGT ACC ATT GAC TTC CCA GAA ATG GT 3' (SEQ ID NO: 60) |
| | | b | CAL-10 | 5' A GAC CAT TTC TGG GAA GTC AAT GGT ACC ATT ACC ATC AGC GT 3' (SEQ ID NO: 61) |
| pAM19 | DKDGNGYISAAE (SEQ ID NO: 62) (calmodulin EF hand loop sequence [III]-derived) | a | CAL-7 | 5' CTA GAT AAG GAT GGC AAT GGC TAT ATC AGT GCT GCA GAA ATG GT 3' (SEQ ID NO: 63) |
| | | b | CAL-8 | 5' AGA CCA TTT CTG CAG CAC TGA TAT AGC CAT TGC CAT CCT TAT 3' (SEQ ID NO: 64) |
| pAM25 | DIDGDGQVNYEE (SEQ ID NO: 65) (calmodulin EF hand loop sequence [IV]-derived) | a | CAL-11 | 5' CTA GAT ATC GAT GGA GAT GGC CAA GTT AAC TAC GAA GAA ATG GT 3' (SEQ ID NO: 66) |
| | | b | CAL-12 | 5' A GAC CAT TTC TTC GTA GTT AAC TTG GCC ATC TCC ATC GAT AT 3' (SEQ ID NO: 67) |
| pAM16 | DFDKDGAITRMD (SEQ ID NO: 68) (SCBP EF hand loop sequence [I]-derived) | a | SCBP-1 | 5' CTA GAT TTC GAC AAG GAT GGA GCC ATC ACG CGT ATG GAC ATG GT 3' (SEQ ID NO: 69) |
| | | b | SCBP-2 | 5' AGA CCA TGT CCA TAC GCG TGA TGG CTC CAT CCT TGT CGA AAT 3' (SEQ ID NO: 70) |
| pAM35 | DKNHNGAISLDE (SEQ ID NO: 71) (aequorin EF hand loop sequence [I]-derived) | a | Aq-13 | 5' CTA GAT AAA AAC CAC AAT GGA GCG ATA TCT CTT GAC GAG ATG GT 3' (SEQ ID NO: 72) |
| | | b | Aq-14 | 5' A GAC CAT CTC GTC AAG AGA TAT CGC TCC ATT GTG GTT TTT AT 3' (SEQ ID NO: 73) |
| pAM36 | DRNHNGKISLDE (SEQ ID NO: 74) (aequorin EF hand loop sequence [I]-derived) | a | Aq-15 | 5' CTA GAT CGC AAC CAC AAT GGA AAG ATA TCT CTT GAC GAG ATG GT 3' (SEQ ID NO: 75) |
| | | b | Aq-16 | 5' A GAC CAT CTC GTC AAG AGA TAT CTT TCC ATT GTG GTT GCG AT 3' (SEQ ID NO: 76) |
| pAM37 | DVNHNGAISLDE (SEQ ID NO: 77) (aequorin EF hand loop sequence [I]-derived) | a | Aq-17 | 5' CTA GAT GTC AAC CAC AAT GGA GCG ATA TCT CTT GAC GAG ATG GT 3' (SEQ ID NO: 78) |
| | | b | Aq-18 | 5' A GAC CAT CTC GTC AAG AGA TAT CGC TCC ATT GTG GTT GAC AT 3' (SEQ ID NO: 79) |
| pAM38 | DRNHNGAISLDE (SEQ ID NO: 80) (aequorin EF hand loop sequence [I]-derived) | a | Aq-19 | 5' CTA GAT CGC AAC CAC AAT GGA GCG ATA TCT CTT GAC GAG ATG GT 3' (SEQ ID NO: 81) |
| | | b | Aq-20 | 5' A GAC CAT CTC GTC AAG AGA TAT CGC TCC ATT GTG GTT GCG AT 3' (SEQ ID NO: 82) |
| pAM39 | DKNHNGKISLDE (SEQ ID NO: 83) (aequorin EF hand loop sequence [I]-derived) | a | Aq-21 | 5' CTA GAT AAA AAC CAC AAT GGA AAG ATA TCT CTT GAC GAG ATG GT 3' (SEQ ID NO: 84) |
| | | b | Aq-22 | 5' A GAC CAT CTC GTC AAG AGA TAT CTT TCC ATT GTG GTT TTT AT 3' (SEQ ID NO: 85) |

(3) Expression of Mutant Apoaequorin in *Escherichia Coli* and Comparison in Half Decay Time of Luminescence To express in *Escherichia coli* the mutant apoaequorin expression vector having the replaced other EF hand loop sequence which was constructed in (2) above, the mutant apoaequorin expression vector was transfected to *Escherichia coli* JM83 in a conventional manner. The transformants obtained were inoculated into 10 ml of LB liquid medium (10 g of bacto-tryptone, 5 g of yeast extract and 5 g of sodium chloride, per liter of water, pH 7.2) containing ampicillin (50 µg/ml) and cultured at 37° C. for 18 hours. The collected culture cells corresponding to 1 ml was suspended in 1 ml of 30 mM Tris-HCl (pH 7.6) containing 10 mM EDTA and then ultrasonicated (Sonifier Model Cycle 250, manufactured by Branson Corp.) for 5 seconds under cooling conditions on ice to yield the extracts of recombinant mutant apoaequorin. Subsequently, 2-mercaptoethanol (1 µl) (manufactured by Wako Pure Chemical Industry) and a solution of substrate coelenterazine in ethanol (1 µg/µl) (JNC Corporation, hereinafter the same) were mixed with the recombinant mutant apoaequorin extract. The mixture was allowed to stand on ice (4° C.) for 18 hours thereby to regenerate into the mutant aequorin. The regeneration reaction mixture was diluted 2-fold with TBS (2 mM Tris-HCl (pH 7.6) containing 15 mM sodium chloride) containing 0.1% (w/v) BSA (manufactured by Sigma Inc.) and 10 mM EDTA. Then, 100 µl of 50 mM calcium solution in 50 mM Tris-HCl (pH 7.6) was added to 10 µl or 100 µl of each regeneration photoprotein solution to start the luminescence reaction. The luminescence activity was measured on a luminescence plate reader Centro LB960 (manufactured by Berthold Inc.) for 30 seconds. The final calcium level in the reaction solution was 25 mM. The luminescence activity was expressed by relative activity (%) to the maximum intensity ($I_{max}$). The results are summarized in TABLE 3 below.

Therefore, a further attempt was made by site-directed mutagenesis at the amino acid sequences of the loop region of EF hand I in native aequorin. In the loop of EF hand I in

TABLE 3

Relative Luminescence Activity and Half Decay Time of Replaced EF Hand [I] Loop Portion-Having Expression Mutant Aequorin Constructed in EXAMPLE 1

| Vector | EF Hand Loop [I] Sequence (basic amino acids are underlined) X * Y * Z G # I-X * *-Z | Relative Luminescence Activity (%) | Half Decay Time (sec.) |
|---|---|---|---|
| pAM2 + | XD V N H N G K I S L D E (SEQ ID NO: 13) | 100.0 | 1.3 |
| pAM20 | D K D Q N G A I T L D E (SEQ ID NO: 14) | 37.0 | 13.5 |
| pAM21 | D I D E S G Q L D V D E (SEQ ID NO: 17) | 0.22 | 1.2 |
| pAM15 | D I N G D G K I T L D E (SEQ ID NO: 20) | 254.7 | 2.1 |
| pAM22 | D K D G S G S I S L D E (SEQ ID NO: 23) | 0.05 | 21.9 |
| pAM23 | D L D N S G K L D V D E (SEQ ID NO: 26) | 0.10 | 4.1 |
| pAM27 | D I N G N G K I T L D E (SEQ ID NO: 29) | 205.7 | 1.2 |
| pAM28 | D K D G S G S I S L D E (SEQ ID NO: 32) | 1.53 | 21.9 |
| pAM29 | D L D N S G K L D V D E (SEQ ID NO: 35) | 0.04 | 1.7 |
| pAM30 | D I N S N G Q I N L N E (SEQ ID NO: 38) | 12.0 | 1.3 |
| pAM31 | D K D R N G S V S L D E (SEQ ID NO: 41) | 3.72 | 11.3 |
| pAM32 | D L D G D G K L D V D E (SEQ ID NO: 44) | 0.02 | 1.6 |
| pAM17 | D V T G D G F T S R E D (SEQ ID NO: 47) | 0.45 | 1.3 |
| pAM33 | D T D K D G Y V S L P E (SEQ ID NO: 50) | 0.57 | 5.5 |
| pAM34 | D F N K N G Q I S R D E (SEQ ID NO: 53) | 0.01 | 1.2 |
| pAM7 | D K D G D G T I T T K E (SEQ ID NO: 56) | 0.01 | 1.7 |
| pAM24 | D A D G N G T I D F P E (SEQ ID NO: 59) | 0.01 | 1.2 |
| pAM19 | D K D G N G Y I S A A E (SEQ ID NO: 62) | 0.36 | 6.3 |
| pAM25 | D I D G D G Q V N Y E E (SEQ ID NO: 65) | 0.05 | 1.0 |
| pAM16 | D F D K D G A I T R M D (SEQ ID NO: 68) | 0.08 | 1.9 |

The foregoing results reveal that the half decay time (time period until the luminescence intensity reaches half of the maximum luminescence intensity) in the aequorin mutants prepared using the mutant apoaequorin produced using the expression vectors pAM20, pAM22, pAM23, pAM28, pAM31, pAM33 and pAM19, wherein the EF hand loop sequence of aequorin was replaced by the loop sequence of EF hands in different calcium-binding proteins, was markedly prolonged by comparison with that of native aequorin. Many of the mutants having long half decay time with twice or more than native aequorin have lysine at the second amino acid residue and arginine at the fourth amino acid residue in the EF hand loop sequences of the mutants and both are basic amino acids, and so on.

aequorin, the replacement of the second valine residue by basic amino acid lysine residue or arginine residue, and the replacement of the 7th lysine residue by alanine residue were performed by the same procedure as described in (2) above.

The results are shown in TABLE 4. In the mutants wherein the second valine residue in the loop of EF hand I of aequorin was replaced by basic amino acid lysine or arginine, clearly the half decay time was markedly prolonged to 5.3 to 11.5 seconds when compared to 1.3 seconds of native aequorin, as shown in TABLE 4. By replacing the 7th lysine residue with the alanine residue, the half decay time was also prolonged to 1.7 seconds. This is considered to be because the fourth amino acid residue is basic amino acid histidine.

TABLE 4

Luminescence Activity and Half Decay Time of Aequorin Mutants Constructed by Site-Directed Mutagenesis into EF Hand [I] Loop Portion of Aequorin

| Vector | Amino Acid Site Mutated in Loop Portion of EF Hand I of Aequorin (underlined) X * Y * Z G # I-X * *-Z | Relative Luminescence Activity (%) | Half Decay Time (sec.) |
|---|---|---|---|
| pAM2 + | X D V N H N G K I S L D E (SEQ ID NO: 13) | 100.0 | 1.3 |
| pAM37 | D V N H N G <u>A</u> I S L D E (SEQ ID NO: 77) | 49.7 | 1.7 |
| pAM35 | D <u>K</u> N H N G <u>A</u> I S L D E (SEQ ID NO: 71) | 73.0 | 11.5 |
| pAm39 | D <u>K</u> N H N G K I S L D E (SEQ ID NO: 83) | 132.4 | 6.9 |
| pAM36 | D <u>R</u> N H N G K I S L D E (SEQ ID NO: 74) | 139.8 | 5.3 |
| pAM38 | D <u>R</u> N H N G <u>A</u> I S L D E (SEQ ID NO: 80) | 66.0 | 7.9 |

Example 2

Construction of Novel Expression Vector piP-H-AM20

AM20 having a longer half decay time and a sufficient luminescence activity was chosen from the aequorin mutants as a representative example and provided for protein purification to analyze the properties.

(1) Construction of Expression Basic Vector piP-H-XEL

The basic vector piP-H-XEL having the histidine sequence at the amino terminus, followed by the multiple cloning site sequence (NcoI/HindIII/NdeI/SacI/KpnI/XhoI/BamHI/EcoRI/SalI/PstI/XbaI/BamHI) was constructed by removing the XbaI site and EcoRI site of piP-His-HE described in Inouye, S. and Hosoya, T. Biochem. Biophys. Res. Comum. (2009) 386: 617-622 and inserting the chemically synthesized multicloning site sequence. The HindIII/EcoRI fragment of the vector pAM20 constructed in EXAMPLE 1 was inserted into the HindIII/EcoRI site of this expression basic vector piP-H-XEL to construct the novel expression vector piP-H-AM20.

Specifically, piP-His-HE was digested with the restriction enzyme XbaI in a conventional manner, then blunt-ended with Klenow fragment (manufactured by Wako Pure Chemical Industry) and ligated to construct the XbaI site-deleted vector piP-H-X. This piP-H-X was digested with the restriction enzymes EcoRI/HindIII, and the following linkers ΔE/H-His6-F and ΔE/H-His6-R, prepared unable to cleave the EcoRI site, were inserted to construct the XbaI site and EcoRI site-deleted vector piP-H-XE.

ΔE/H-His6-F
(SEQ ID NO: 86)
(5' AAT TcC CAC CAT CAC CAT CAC CAT GGT A 3')

ΔE/H-His6-R
(SEQ ID NO: 87)
(5' AG CTT ACC ATG GTG ATG GTG ATG GTG GA 3')

The piP-H-XE vector was further digested with the restriction enzymes HindIII/BamHI, and then the following linkers: Linker F(11)H-B and Linker R(11)H-B, which are multicloning sequences, were inserted to construct the novel expression basic vector piP-H-XEL.

Linker F(11)H-B
(SEQ ID NO: 88)
(5' AG CTT CAT ATG GAG CTC GGT ACC CTC GAG GGA TCC GAA TTC GTC GAC CTG CAG TCT AGA G 3')

Linker R(11)H-B
(SEQ ID NO: 89)
(5' GA TCC TCT AGA CTG CAG GTC GAC GAA TTC GGA TCC CTC GAG GGT ACC GAG CTC CAT ATG A 3')

The expression basic vector is controlled by the lipoprotein promoter and the lactose operator in *Escherichia coli*, and has an OmpA sequence for secretion, a six histidine sequence for purification with chelate gel, and multiple cloning sequences (NcoI/HindIII/NdeI/SacI/KpnI/XhoI/BamHI/EcoRI/SalI/PstI/XbaI/BamHI).

(2) Construction of Novel Expression Vector piP-H-AM20

Figure 2:
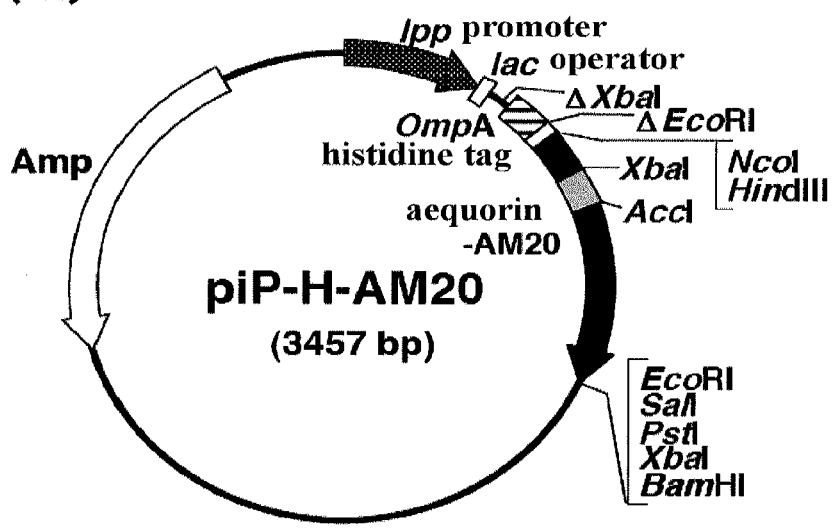
FIG. 2(a) is a schematic view showing the recombinant mutant aequorin (AM20) expression vector piP-H-AM20.
FIG. 2(b) shows a representative amino acid sequence of the OmpA-histidine tag-mutant aequorin-AM20 portion of the piP-H-AM20 expression vector where the amino acid sequence of the mutant apoaequorin is that of SEQ ID NO: 6 (188 a.a.).

The vector pAM20 constructed in EXAMPLE 1 was digested with the restriction enzymes HindIII/EcoRI and the resulting fragment was inserted into the restriction enzyme HindIII/EcoRI site of the basic vector piP-H-XEL constructed in (1) above to construct the expression vector piP-H-AM20 shown in FIG. 2. The DNA sequence encoding the recombinant mutant aequorin AM20 inserted into the expression vector piP-H-AM20 is shown by SEQ ID NO: 7. Also, the amino acid sequence of the recombinant mutant aequorin (AM20) inserted into the expression vector piP-H-AM20 is shown by SEQ ID NO: 8. The DNA sequence (the 94th to 657th sequence of SEQ ID NO: 7) encoding the mutant apoaequorin is shown by SEQ ID NO: 5. Also, the amino acid sequence (the 32nd to 219th sequence of SEQ ID NO: 8) of the mutant apoaequorin encoded by the DNA sequence of SEQ ID NO: 5 is shown by SEQ ID NO: 6.

Example 3

Expression and Purification of Recombinant Mutant Aequorin AM20

The recombinant mutant aequorin AM20 was obtained as described below. Using the expression vector piP-H-AM20, the recombinant mutant apoaequorin AM20 was expressed in *Escherichia coli* and purified by nickel chelate column chromatography to yield the recombinant mutant apoaequorin AM20. The purified recombinant mutant apoaequorin AM20 was incubated with substrate coelenterazine under reducing conditions to yield the purified recombinant mutant aequorin AM20.

(1) Expression of Recombinant Mutant Apoaequorin AM20 in *Escherichia coli*

To express the recombinant mutant apoaequorin AM20 in *Escherichia coli*, the mutant apoaequorin gene expression vector piP-H-AM20 was used. The vector was transformed into *Escherichia coli* strain WA802 in a conventional manner. The resulting transformants were inoculated into 10 ml of LB liquid medium (10 g of bacto-tryptone, 5 g of yeast extract and 5 g of sodium chloride, per liter of water, pH 7.2) containing ampicillin (50 μg/ml) and cultured at 25° C. for 18 hours. The culture broth was then added to 5 vessels holding 400 mL each of fresh LB liquid medium (2 liters in total amount) and cultured at 37° C. for 18 hours. After completion of the culture, the cells were collected by centrifugation (5,000 rpm, 5 minutes) to yield the starting material for protein extraction.

(2) Extraction of Recombinant Mutant Apoaequorin AM20 from Culture Cells and Nickel Chelate Column Chromatography The culture cells collected were suspended in 200 ml of 50 mM Tris-HCl (pH 7.6) and ultrasonicated (manufactured by Branson, Sonifier Model Cycle 250) 3 times for 3 minutes under cooling conditions on ice. The cell debris was then centrifuged at 10,000 rpm (12,000×g) at 4° C. for 20 minutes. The resulting soluble fraction was applied to a nickel chelate column (manufactured by Amersham Bioscience; column size: 2.5 in diameter×6.5 cm) to adsorb the recombinant mutant apoaequorin AM20. After washing with 300 ml of 50 mM Tris-HCl (pH 7.6), the recombinant mutant apoaequorin AM20 was eluted with 30 ml of 50 mM Tris-HCl (pH 7.6) containing 0.1M imidazole. From 2 L of the cultured cells, 44.8 mg of the purified recombinant mutant apoaequorin AM20 was obtained.

(3) Regeneration from Recombinant Mutant Apoaequorin AM20 to Recombinant Mutant Aequorin AM20

Regeneration from the recombinant mutant apoaequorin AM20 to the recombinant mutant aequorin AM20 was performed under the following conditions.

In 90 ml of 50 mM Tris-HCl (pH 7.6) containing 10 mM DTT and 10 mM EDTA was dissolved 10 ml of the purified recombinant mutant apoaequorin AM20 obtained in (2) above. A solution of 0.3 mg of coelenterazine in ethanol was added to the solution. The solution mixture was allowed to stand at 4° C. overnight to regenerate to the recombinant mutant aequorin AM20.

(4) Purification of Recombinant Mutant Aequorin AM20 by Butyl Sepharose Column Chromatography The recombinant mutant aequorin AM20 which formed a complex with coelenterazine was separated from the recombinant mutant apoaequorin AM20 which did not form the complex, by hydrophobic chromatography using Butyl Sepharose 4 Fast Flow Gel (manufactured by Amersham Bioscience).

Specifically, the recombinant mutant aequorin AM20 (130 ml) obtained in (3) above was adjusted to a final ammonium sulfate concentration of 2M. Next, the insoluble fraction was removed by centrifugation at 10,000 rpm (12,000×g) at 4° C. for 20 minutes. The supernatant was applied and applied onto a Butyl Sepharose 4 Fast Flow Gel column (column size: 1.5 in diameter×3.2 cm), which had been equilibrated with 10 mM Tris-HCl (pH 7.6) containing 2M ammonium sulfate and 2 mM EDTA. After washing with 70 ml of 10 mM Tris-HCl (pH 7.6) containing 2M-ammonium sulfate and 2 mM EDTA, the recombinant mutant aequorin AM20 was eluted with 20 ml of 10 mM Tris-HCl (pH 7.6) containing 1.2M-ammonium sulfate and 2 mM EDTA.

The protein concentration was determined with a commercial assay kit (manufactured by BioRad) by the method of Bradford, using bovine serum albumin (manufactured by Pierce Biotechnology) as a standard. As a result, the recovery of activity and protein yield of the recombinant mutant apoaequorin AM20 were 91.9% and 44.8 mg, respectively, by nickel chelate column chromatography from 2 L of the cultured cells, as shown in TABLE 5. From the apoprotein obtained, 10.4 mg was regenerated to the recombinant mutant aequorin AM20, which was then purified by the butyl Sepharose column chromatography. As a result, the recovery of activity and protein yield of the recombinant mutant aequorin AM20 were 13.0% and 0.45 mg, respectively.

TABLE 5

Purification Yield of Recombinant Mutant Aequorin AM20

| Purification Step | Total Volume (ml) | Total Protein (mg) | Total Activity ($\times 10^{10}$ rlu) | Specific Activity ($\times 10^{10}$ rlu/mg) | Recovery (%) Protein | Recovery (%) Activity |
|---|---|---|---|---|---|---|
| Crude extract | 200 | 570 | 51.2 | 0.09 | 100 | 100 |
| Nickel chelate column | 30 | 44.8 | 47.1 | 1.05 | 7.9 | 91.9 |
| Regeneration to recombinant mutant aequorin AM20 | 130 | 10.4 | 2.3 | 0.22 | 100 | 100 |
| Butyl Sepharose column | 20 | 0.45 | 0.3 | 0.66 | 4.3 | 13.0 |

Example 4

Measurement of Luminescence Activity

The luminescence activity during the purification steps of the recombinant mutant apoaequorin AM20 was measured as follows. After 1 ml of 30 mM Tris-HCl (pH 7.6) containing 10 mM EDTA was mixed with 2-mercaptoethanol (1 μl) and a solution of substrate coelenterazine (1 μg/μl) in ethanol, 10 μl of the recombinant mutant apoaequorin AM20 was added to the mixture and stood for 2 hours on ice (4° C.). To 1 μl of the regeneration reaction solution was added 100 μl of 50 mM calcium solution in 50 mM Tris-HCl (pH 7.6) to start the luminescence reaction. The luminescence activity was measured using a luminometer Luminescencer-PSN AB2200 (manufactured by Atto Company) and expressed as the maximum intensity ($I_{max}$).

Example 5

Preparation of Purified Aequorin

Apoaequorin was prepared by expressing the apoaequorin expression vector piP-His-HE and purifying in accordance with the method described in Inouye, S. and Hosoya, T. Biochem Biophys Res Comum. (2009) 386: 617-622. Regeneration from apoaequorin to aequorin was achieved by the method described in Shimomura, O. and Inouye, S. Protein Express Purifi. (1999) 16, 91-95.

Example 6

Bioluminescence Spectra of Purified Aequorin and Mutant Aequorin AM20 and Spectroscopic Comparative Analysis To 1 ml of an aqueous solution containing the purified aequorin or the recombinant mutant aequorin AM20 was added 100 µl of 10 mM calcium chloride solution in 50 mM Tris-HCl (pH 7.6) to emit light. The luminescence spectra were measured in a quartz cell having a 10 mm optical path using a fluorescence spectrophotometer (JASCO FP-6500) with the excitation source turned off. The measurement was performed under the following conditions: bandpass, 3 nm; response, 0.5 second; scan speed, 2000 nm/minute; 22 to 25° C. After the luminescence reaction solution by addition of the calcium solution was allowed to stand at 22 to 25° C. for an hour, the fluorescence spectra were measured in a quartz cell having a 10 mm optical path. The measurement conditions were excitation wavelength: 330 nm, bandpass: 3 nm, response: 0.5 sec, scan speed: 1000 nm/min; 22 to 25° C.

The luminescence and fluorescence spectra measured were corrected and the luminescence maximum (λmax) and half bandwidth (nm) were determined, which are shown in TABLE 6. The luminescence spectra of the purified aequorin and the recombinant mutant aequorin AM20 as well as the fluorescence spectra following the luminescence spectra were almost the same. The results suggest that both light emission processes would be the same and the blue fluorescent proteins formed after the luminescence reaction have almost the same structure.

TABLE 6

Results of Analysis of Spectra from Purified Aequorin and Recombinant Mutant Aequorin AM20

| Analysis of Spectra | Bioluminescence Spectra | | Fluorescence Spectra after Bioluminescence (excited at 330 nm) | |
|---|---|---|---|---|
| | Luminescence Maximum (λmax) | Half Bandwidth (nm) | Fluorescence Maximum (λmax) | Half Bandwidth (nm) |
| Aequorin | 468.0 | 93.3 | 471.5 | 93.3 |
| Mutant aequorin AM20 | 471.5 | 94.5 | 475.5 | 96.9 |

Example 7

Figure 3:
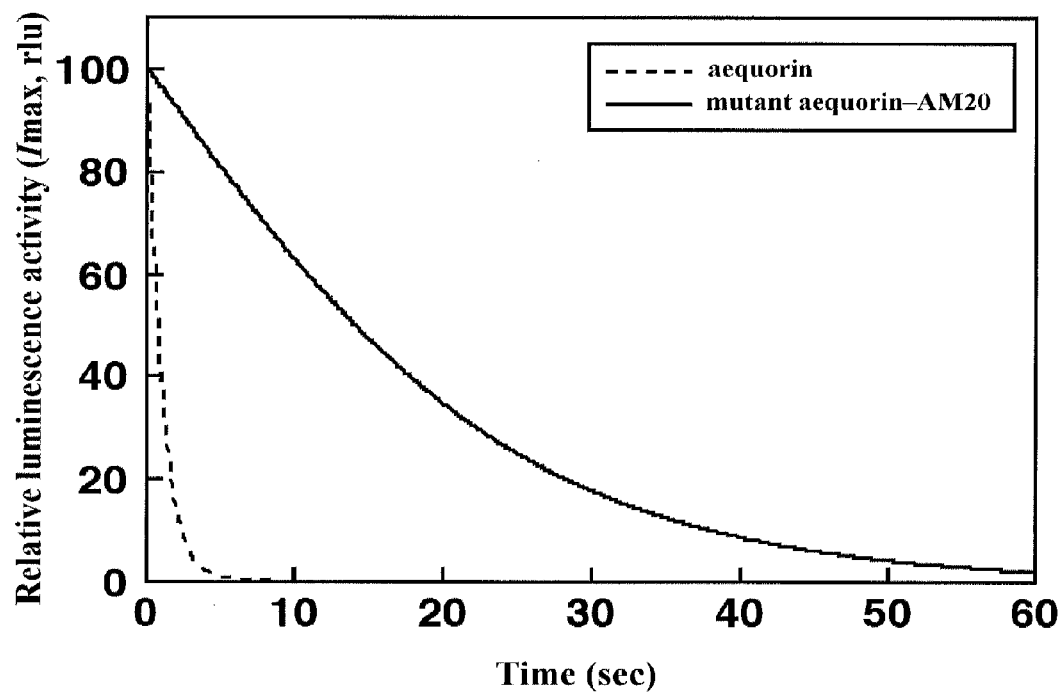
FIG. 3 shows the luminescence patterns of purified aequorin and purified recombinant mutant aequorin (AM20), wherein the dotted line represents the luminescence pattern of aequorin and the solid line represents the luminescence pattern of the recombinant mutant aequorin (AM20).

Measurement of Luminescence Patterns of Purified Aequorin and Recombinant Mutant Aequorin AM20 and Comparison in Half Decay Times A luminescence plate reader Centro LB960 (manufactured by Berthold) was used to compare luminescence patterns of the purified aequorin and the recombinant mutant aequorin AM20 and to determine their half decay times. More specifically, 10 µl (2.5 ng) of the purified aequorin or 10 µl (9 ng) of the purified mutant aequorin AM20, both diluted in TBS containing 0.1% (w/v) BSA and 10 mM EDTA, was added to 50 µl of 50 mM Tris-HCl (pH 7.6) containing 10 mM calcium chloride to start the luminescence reaction. The luminescence activity was measured for 60 seconds in 0.1 second intervals and expressed by relative activity (%) to the maximum intensity ($I_{max}$). The luminescence patterns are shown in FIG. 3. The half decay time of luminescence was also determined based on the luminescence patterns measured (FIG. 3), and compared between aequorin and the recombinant mutant aequorin AM20, which are shown in TABLE 7. It was revealed that the recombinant mutant aequorin AM20 had a longer decay time and its half decay time was approximately 10 times or more, when compared to aequorin. This tendency is the same as the half decay time determined in EXAMPLE 1 using the mutant apoaequorin extract. It was revealed that the mutant aequorin AM20 had obviously a longer half decay time.

TABLE 7

Half Decay Time of Luminescence by Purified Recombinant Aequorin and Purified Recombinant Mutant Aequorin AM20

| Photoprotein | Half Decay Time of Luminescence (sec) |
|---|---|
| Aequorin | 0.90 |
| Mutant aequorin AM20 | 14.12 |

Example 8

Substrate Specificity of Recombinant Mutant Aequorin AM20

It is reported that semi-synthetic aequorin can be produced using apoaequorin and the coelenterazine analogue. The mutant semi-synthetic aequorin AM20 was prepared to examine the properties. Specifically, 1 ml of 30 mM Tris-HCl (pH 7.6) containing 10 mM EDTA was mixed with 2-mercaptoethanol (1 µl) and a solution of the coelenterazine analogue (1 µg/µl) dissolved in ethanol. Then, 10 µl of the purified apoaequorin or recombinant mutant apoaequorin AM20 was added to the mixture, which was allowed to stand on ice (4° C.) for 5 hours to perform the regeneration reaction. To 5 µl of the regeneration mixture which was diluted 10-fold in TBS containing 0.1% (w/v) BSA and 10 mM EDTA was added 100 µl of 50 mM calcium solution in 50 mM Tris-HCl (pH 7.6) to start the luminescence reaction. The luminescence activity was measured on a luminescence plate reader Centro LB960 (manufactured by Berthold Inc.) for 60 seconds in 0.1 second intervals and expressed by relative activity (%) to the maximum intensity ($I_{max}$). The half decay time was determined from the luminescence patterns. The results are summarized in FIG. 8 below.

It is demonstrated that by using the recombinant mutant aequorin AM20 in combination with the coelenterazine analogue, the half decay time was more prolonged 1.5 to 5 times or more than that of coelenterazine (CTZ). It was revealed that especially when n-CTZ, cf3-CTZ, i-CTZ, meo-CTZ and me-CTZ (manufactured by JNC Corporation) serve as the light-emitting substrate, the semi-synthetic aequorin gave an extremely prolonged half decay time of the luminescence. In other words, it is demonstrated that the luminescence time can be further prolonged by use of the mutated aequorin with a longer half decay time and the coelenterazine analogue in combination.

TABLE 8

Prolonged Half Decay Time by Purified Aequorin, Recombinant Mutant Aequorin AM20 and Coelenterazine Analogue

| | Native Aequorin | | | Mutant Aequorin AM20 | | |
|---|---|---|---|---|---|---|
| Coelenterazine Analogue | Relative Luminescence Intensity (%) | Luminescence Intensity for 60 Secs (%) | Half Decay Time (sec) | Relative Luminescence Intensity (%) | Luminescence Intensity for 60 Secs (%) | Half Decay Time (sec) |
| CTZ | 100 | 100 | 0.81 | 100 | 100 | 14.12 |
| Bis-CTZ | 0.0 | 0.0 | — | 0.0 | 0.0 | — |
| h-CTZ | 87.9 | 70.1 | 0.69 | 220 | 45.4 | 2.98 |
| hcp-CTZ | 20.5 | 14.3 | 0.51 | 187 | 7.6 | 0.61 |
| n-CTZ | 3.6 | 24.0 | 4.71 | 1.0 | 1.9 | 44.04 |
| 3iso-CTZ | 51.6 | 13.4 | 0.24 | 224 | 9.2 | 0.66 |
| 3meo-CTZ | 64.9 | 35.6 | 0.52 | 266 | 25.0 | 1.43 |
| cf3-CTZ | 6.3 | 48.6 | 5.95 | 7.5 | 18.6 | >60 |
| i-CTZ | 5.0 | 65.3 | 11.42 | 3.6 | 9.8 | >60 |
| et-CTZ | 27.3 | 44.1 | 1.21 | 56.7 | 33.6 | 1.94 |
| meo-CTZ | 22.3 | 60.1 | 1.63 | 26.6 | 35.6 | 18.35 |
| me-CTZ | 5.8 | 45.0 | 5.00 | 6.8 | 15.4 | >60 |
| 3me-CTZ | 35.0 | 21.2 | 0.51 | 125 | 35.5 | 3.69 |
| αmeh-CTZ | 2.2 | 0.9 | 0.35 | 19.4 | 0.9 | 0.61 |

Example 9

Determination of Calcium Concentration by Purified Aequorin and Recombinant Mutant Aequorin AM20

Figure 4:
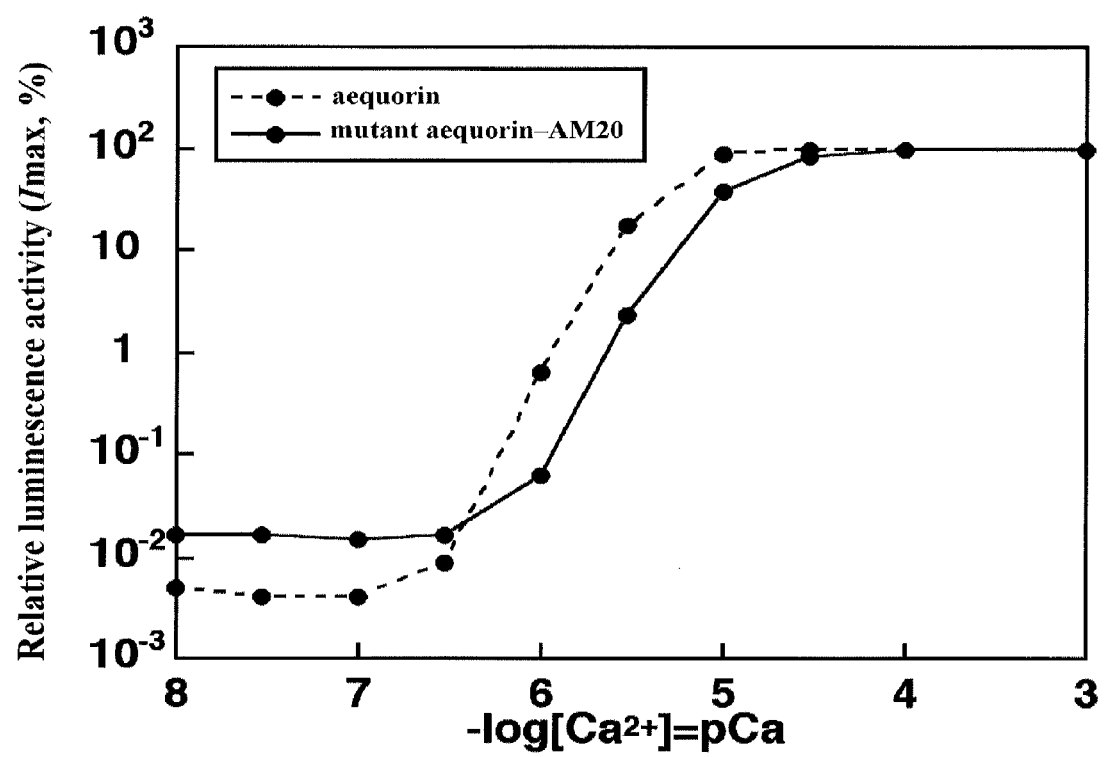
FIG. 4 shows detection limit of calcium ions using the purified aequorin and the purified recombinant mutant aequorin (AM20). The dotted line denotes detection limit of calcium ions in aequorin. The solid line denotes detection limit of calcium ions in the recombinant mutant aequorin (AM20).

To 50 µl of calcium standard solution (0.001 mM, 0.003 mM, 0.01 mM, 0.03 mM, 0.1 mM, 0.3 mM, 1 mM, 3 mM, 10 mM, 30 mM or 100 mM) (manufactured by Wako Pure Chemical Industry) was added 10 µl (2.5 ng) of a solution of the purified aequorin or 10 µl (9 ng) of a solution of the recombinant mutant aequorin AM20, both diluted in TBS containing 0.1% (w/v) BSA and 10 mM EDTA to start the luminescence reaction. The luminescence activity was measured for 60 seconds on a luminescence plate reader Centro LB960 (manufactured by Berthold) and expressed by relative activity (%) to the maximum intensity ($I_{max}$) (FIG. 4).

It became clear that the recombinant mutant aequorin AM20 was less sensitive to calcium when compared to aequorin. It was demonstrated that the lower sensitivity to calcium resulted in a longer half decay time of the recombinant mutant aequorin AM20.

Sequence Listing Free Text

[SEQ ID NO: 1] shows the nucleotide sequence of DNA encoding apoaequorin.
[SEQ ID NO: 2] shows the amino acid sequence of apoaequorin encoded by the nucleotide sequence of SEQ ID NO: 1.
[SEQ ID NO: 3] shows the nucleotide sequence of DNA encoding the recombinant apoaequorin inserted into the expression vector pAM2+X.
[SEQ ID NO: 4] shows the amino acid sequence of the recombinant apoaequorin encoded by the nucleotide sequence of SEQ ID NO: 3.
[SEQ ID NO: 5] shows the nucleotide sequence (the 94th to 657th sequence of SEQ ID NO: 7) encoding the mutant apoaequorin.
[SEQ ID NO: 6] shows the amino acid sequence (the 32nd to 219th sequence of SEQ ID NO: 8) of the mutant apoaequorin encoded by the nucleotide sequence of SEQ ID NO: 5.
[SEQ ID NO: 7] shows the nucleotide sequence of the recombinant mutant apoaequorin (AM20) inserted into the expression vector piP-H-AM20.
[SEQ ID NO: 8] shows the amino acid sequence of the recombinant mutant apoaequorin (AM20) encoded by the nucleotide sequence of SEQ ID NO: 7.
[SEQ ID NO: 9] shows the nucleotide sequence of primer RV-M.
[SEQ ID NO: 10] shows the nucleotide sequence of primer Aq-2.
[SEQ ID NO: 11] shows the nucleotide sequence of primer Aq-1.
[SEQ ID NO: 12] shows the nucleotide sequence of primer M13-47.
[SEQ ID NO: 13] shows the amino acid sequence of aequorin EF hand loop [I] (pAM2+X).
[SEQ ID NO: 14] shows the amino acid sequence of aequorin EF hand loop [III] (pAM20).
[SEQ ID NO: 15] shows the nucleotide sequence of primer Aq-9.
[SEQ ID NO: 16] shows the nucleotide sequence of primer Aq-10.
[SEQ ID NO: 17] shows the amino acid sequence of aequorin EF hand loop [IV] (pAM21).
[SEQ ID NO: 18] shows the nucleotide sequence of primer Aq-11.
[SEQ ID NO: 19] shows the nucleotide sequence of primer Aq-12.
[SEQ ID NO: 20] shows the amino acid sequence of clytin-I EF hand loop [I] (pAM15).
[SEQ ID NO: 21] shows the nucleotide sequence of primer PH-52.
[SEQ ID NO: 22] shows the nucleotide sequence of primer PH-53.
[SEQ ID NO: 23] shows the amino acid sequence of clytin-I EF hand loop [III] (pAM22).
[SEQ ID NO: 24] shows the nucleotide sequence of primer PH-55.
[SEQ ID NO: 25] shows the nucleotide sequence of primer PH-56.
[SEQ ID NO: 26] shows the amino acid sequence of clytin-I EF hand loop [IV] (pAM23).

[SEQ ID NO: 27] shows the nucleotide sequence of primer PH-57.
[SEQ ID NO: 28] shows the nucleotide sequence of primer PH-58.
[SEQ ID NO: 29] shows the amino acid sequence of clytin-II EF hand loop [I] (pAM27).
[SEQ ID NO: 30] shows the nucleotide sequence of primer PH-59.
[SEQ ID NO: 31] shows the nucleotide sequence of primer PH-60.
[SEQ ID NO: 32] shows the amino acid sequence of clytin-II EF hand loop [III] (pAM28).
[SEQ ID NO: 33] shows the nucleotide sequence of primer PH-61.
[SEQ ID NO: 34] shows the nucleotide sequence of primer PH-62.
[SEQ ID NO: 35] shows the amino acid sequence of clytin-II EF hand loop [IV] (pAM29).
[SEQ ID NO: 36] shows the nucleotide sequence of primer PH-63.
[SEQ ID NO: 37] shows the nucleotide sequence of primer PH-64.
[SEQ ID NO: 38] shows the amino acid sequence of mitrocomin EF hand loop [I] (pAM30).
[SEQ ID NO: 39] shows the nucleotide sequence of primer MI-1.
[SEQ ID NO: 40] shows the nucleotide sequence of primer MI-2.
[SEQ ID NO: 41] shows the amino acid sequence of mitrocomin EF hand loop [III] (pAM31).
[SEQ ID NO: 42] shows the nucleotide sequence of primer MI-3.
[SEQ ID NO: 43] shows the nucleotide sequence of primer MI-4.
[SEQ ID NO: 44] shows the amino acid sequence of mitrocomin EF hand loop [IV] (pAM32).
[SEQ ID NO: 45] shows the nucleotide sequence of primer MI-5.
[SEQ ID NO: 46] shows the nucleotide sequence of primer MI-6.
[SEQ ID NO: 47] shows the amino acid sequence of RLBP EF hand loop [I] (pAM17).
[SEQ ID NO: 48] shows the nucleotide sequence of primer RLBP-4.
[SEQ ID NO: 49] shows the nucleotide sequence of primer RLBP-5.
[SEQ ID NO: 50] shows the amino acid sequence of RLBP EF hand loop [III] (pAM33).
[SEQ ID NO: 51] shows the nucleotide sequence of primer RLBP-6.
[SEQ ID NO: 52] shows the nucleotide sequence of primer RLBP-7.
[SEQ ID NO: 53] shows the amino acid sequence of RLBP EF hand loop [IV] (pAM34).
[SEQ ID NO: 54] shows the nucleotide sequence of primer RLBP-8.
[SEQ ID NO: 55] shows the nucleotide sequence of primer RLBP-9.
[SEQ ID NO: 56] shows the amino acid sequence of calmodulin EF hand loop [I] (pAM7).
[SEQ ID NO: 57] shows the nucleotide sequence of primer CAL-1.
[SEQ ID NO: 58] shows the nucleotide sequence of primer CAL-2.
[SEQ ID NO: 59] shows the amino acid sequence of calmodulin EF hand loop [II] (pAM24).
[SEQ ID NO: 60] shows the nucleotide sequence of primer CAL-9.
[SEQ ID NO: 61] shows the nucleotide sequence of primer CAL-10.
[SEQ ID NO: 62] shows the amino acid sequence of calmodulin EF hand loop [III] (pAM19).
[SEQ ID NO: 63] shows the nucleotide sequence of primer CAL-7.
[SEQ ID NO: 64] shows the nucleotide sequence of primer CAL-8.
[SEQ ID NO: 65] shows the amino acid sequence of calmodulin EF hand loop [IV] (pAM25).
[SEQ ID NO: 66] shows the nucleotide sequence of primer CAL-11.
[SEQ ID NO: 67] shows the nucleotide sequence of primer CAL-12.
[SEQ ID NO: 68] shows the amino acid sequence of SCBP EF hand loop [I] (pAM16).
[SEQ ID NO: 69] shows the nucleotide sequence of primer SCBP-1.
[SEQ ID NO: 70] shows the nucleotide sequence of primer SCBP-2.
[SEQ ID NO: 71] shows the mutated amino acid sequence of aequorin EF hand loop [I] (pAM35).
[SEQ ID NO: 72] shows the nucleotide sequence of primer Aq-13.
[SEQ ID NO: 73] shows the nucleotide sequence of primer Aq-14.
[SEQ ID NO: 74] shows the amino acid sequence of aequorin EF hand loop [I] mutant (pAM36).
[SEQ ID NO: 75] shows the nucleotide sequence of primer Aq-15.
[SEQ ID NO: 76] shows the nucleotide sequence of primer Aq-16.
[SEQ ID NO: 77] shows the amino acid sequence of aequorin EF hand loop [I] mutant (pAM37).
[SEQ ID NO: 78] shows the nucleotide sequence of primer Aq-17.
[SEQ ID NO: 79] shows the nucleotide sequence of primer Aq-18.
[SEQ ID NO: 80] shows the amino acid sequence of aequorin EF hand loop [I] mutant (pAM38).
[SEQ ID NO: 81] shows the nucleotide sequence of primer Aq-19.
[SEQ ID NO: 82] shows the nucleotide sequence of primer Aq-20.
[SEQ ID NO: 83] shows the amino acid sequence of aequorin EF hand loop [I] mutant (pAM39).
[SEQ ID NO: 84] shows the nucleotide sequence of primer Aq-21.
[SEQ ID NO: 85] shows the nucleotide sequence of primer Aq-22.
[SEQ ID NO: 86] shows the nucleotide sequence of linker ΔE/H-His6-F.
[SEQ ID NO: 87] shows the nucleotide sequence of linker ΔE/H-His6-R.
[SEQ ID NO: 88] shows the nucleotide sequence of linker: Linker F(11)H-B.
[SEQ ID NO: 89] shows the nucleotide sequence of linker: Linker R(11)H-B.

The invention claimed is:

1. An isolated mutant apoprotein comprising an amino acid sequence wherein the 23rd to 34th amino acids in the amino acid sequence of SEQ ID NO: 2 are substituted with an amino acid represented by formula I below: Xaa23-Xaa24-Xaa25-Xaa26-Xaa27-Xaa28-Xaa29-Xaa30-Xaa31-Xaa32 Xaa33-Xaa34,
wherein:
Xaa23 is Asp, Glu, Gln, Ser, Thr or Asn,
Xaa24 is Lys, Arg, His, Leu or Thr,
Xaa25 is Asp, Glu, Gln, Ser, Thr or Asn,
Xaa26 is an optional amino acid,
Xaa27 is Asp, Glu, Gln, Ser, Thr or Asn,
Xaa28 is Gly,
Xaa29 is an optional amino acid,
Xaa30 is Ile, Leu or Val,
Xaa31 is Asp, Glu, Gln, Ser, Thr or Asn,
Xaa32 is an optional amino acid,
Xaa33 is an optional amino acid, and,
Xaa34 is Asp, Glu, Gln, Ser, Thr or Asn;
having a function to bind to the peroxide of coelenterazine or the peroxide of a coelenterazine analogue to form a photoprotein capable of emitting light under the action of calcium ions; and,
having a half decay time of the luminescence emitted by binding of the photoprotein to calcium ions being not less than 2 seconds.

2. The isolated mutant apoprotein according to claim 1, wherein in formula I above:
Xaa23 is Asp,
Xaa24 is Lys, Arg, Leu or Thr,
Xaa25 is Asn or Asp,
Xaa26 is His, Gln, Asn, Gly, Arg or Lys,
Xaa27 is Asn, Asp or Ser,
Xaa28 is Gly,
Xaa29 is Ala, Lys, Ser or Tyr,
Xaa30 is Ile, Leu or Val,
Xaa31 is Ser, Thr or Asp,
Xaa32 is Leu, Val or Ala,
Xaa33 is Asp, Pro or Ala, and,
Xaa34 is Glu.

3. The isolated mutant apoprotein according to claim 2, Wherein in formula I above:
Xaa23 is Asp,
Xaa24 is Lys,
Xaa25 is Asp,
Xaa26 is Gln,
Xaa27 is Asn,
Xaa28 is Gly,
Xaa29 is Ala,
Xaa30 is Ile,
Xaa31 is Thr,
Xaa32 is Len,
Xaa33 is Asp, and,
Xaa34 is Glu.

4. The isolated mutant apoprotein according to claim 2, wherein in formula I above:
Xaa23 is Asp,
Xaa24 is Lys or Arg,
Xaa25 is Asn,
Xaa26 is His,
Xaa27 is Asn,
Xaa28 is Gly,
Xaa29 is Ala or Lys,
Xaa30 is Ile,
Xaa31 is Ser,
Xaa32 is Leu,
Xaa33 is Asp, and,
Xaa34 is Glu.

5. The isolated mutant apoprotein according to claim 1, which further contains a secretory signal peptide and/or a peptide for purification.

6. A photoprotein consisting of the isolated mutant apoprotein according to claim 1 and the peroxide of coelenterazine or the peroxide of a coelenterazine analogue.

7. The photoprotein according to claim 6, wherein the coelenterazine analogue is n-coelenterazine, cf3-coelenterazine, i-coelenterazine, meo-coelenterazine or me-coelenterazine.

8. A kit comprising the isolated mutant apoprotein according to claim 1 or a photoprotein consisting of the isolated mutant apoprotein and a peroxide of coelenterazine or a peroxide of a coelenterazine analogue.

9. A method for detecting or determining calcium ions, which comprises the step of measuring a luminescence generated from photoprotein consisting or the isolated mutant apoprotein according to claim 1 and a peroxide of coelenterazine or a peroxide of a coelenterazine analogue in a sample solution or in a cell to detect or determine calcium ions.

10. A method for producing a fluorescent protein, which comprises reacting the isolated mutant apoprotein according to claim 1 with coelenteramide or its analogue in the presence or absence of a calcium ion or a divalent or trivalent ion replaceable for the calcium ion to produce the fluorescent protein.

11. The method according to claim 10, wherein the reaction is performed in the presence of a reducing agent.

12. The method according to claim 10, wherein the reaction is performed in the presence of a chelating agent for removing the calcium ion or the divalent or trivalent ion replaceable for the calcium ion.

13. An isolated mutant apoprotein comprising the amino acid sequence of SEQ ID NO: 8.

* * * * *